(12) United States Patent
Horwitz et al.

(10) Patent No.: US 7,109,341 B2
(45) Date of Patent: Sep. 19, 2006

(54) THERAPEUTIC AMIDES

(75) Inventors: Jerome P. Horwitz, Farmington Hills, MI (US); Thomas H. Corbett, Grosse Pointe Park, MI (US); Eduardo Palomino, Royal Oak, MI (US); Lisa Polin, Oak Park, MI (US); Stuart T. Hazeldine, Taylor, MI (US)

(73) Assignee: Wayne State University, Detroit, MI (US)

( * ) Notice: Subject to any disclaimer, the term of this patent is extended or adjusted under 35 U.S.C. 154(b) by 0 days.

(21) Appl. No.: 10/613,914

(22) Filed: Jul. 3, 2003

(65) Prior Publication Data

US 2004/0132618 A1 Jul. 8, 2004

Related U.S. Application Data

(60) Provisional application No. 60/393,858, filed on Jul. 3, 2002.

(51) Int. Cl.
C07D 215/227 (2006.01)
A61K 31/47 (2006.01)
A01N 41/42 (2006.01)

(52) U.S. Cl. ................ 546/157; 504/235; 504/247

(58) Field of Classification Search ............... 504/235, 504/247; 546/157, 153; 544/354; 514/312
See application file for complete search history.

(56) References Cited

U.S. PATENT DOCUMENTS

| | | | |
|---|---|---|---|
| 4,559,157 A | 12/1985 | Smith et al. | |
| 4,608,392 A | 8/1986 | Jacquet et al. | |
| 4,629,493 A * | 12/1986 | Ura et al. | 504/235 |
| 4,710,507 A | 12/1987 | Campbell et al. | |
| 4,760,066 A * | 7/1988 | Busse et al. | 514/263.32 |
| 4,820,508 A | 4/1989 | Wortzman | |
| 4,938,949 A | 7/1990 | Borch et al. | |
| 4,992,478 A | 2/1991 | Geria | |
| 5,250,690 A * | 10/1993 | Turner et al. | 544/354 |
| 5,364,831 A * | 11/1994 | Ura et al. | 504/235 |
| 6,103,913 A * | 8/2000 | Hay et al. | 549/292 |
| 6,133,457 A * | 10/2000 | Patel | 548/547 |
| 6,160,006 A * | 12/2000 | Edwards et al. | 514/455 |
| 6,197,728 B1 * | 3/2001 | Ura et al. | 504/235 |
| 6,238,644 B1 * | 5/2001 | Rillema | 424/1.61 |
| 6,252,064 B1 * | 6/2001 | Martinelli et al. | 540/454 |
| 6,352,991 B1 * | 3/2002 | Zemlicka et al. | 514/263.37 |
| 6,586,461 B1 * | 7/2003 | Gibbs | 514/438 |
| 6,680,311 B1 * | 1/2004 | Al-Awar et al. | 514/183 |
| 6,703,415 B1 * | 3/2004 | Mobashery et al. | 514/430 |
| 6,747,021 B1 * | 6/2004 | Corbett et al. | 514/183 |
| 6,790,841 B1 * | 9/2004 | Zemlicka et al. | 514/81 |
| 6,867,219 B1 * | 3/2005 | Horwitz et al. | 514/312 |

OTHER PUBLICATIONS

Draetta et al "Section V. Topics in Biology", Annual Reports in Medicinal Chemistry, 31, 1996, Academic Press, San Diego, pp. 241-246.*
Joseph R. Bertino and Sydney E. Salmon "Principles of Cancer Therapy", Oncology XIV, pp. 1060-1074, 21st Edition, vol. 1 (2000), Edited by Lee Goldman, M.D. and J. Claude Bennett, M.D..*
Balasubramanian et al "Recent Developments in Cancer, Etc." Annual Reports in Medicinal Chemistry, 33, 1998, Academ Press, San Diego, pp. 151-159.*
Hazeldine et al "Design, Synthesis, and Biological Evaluation of Analogues of the Antitumor Agent," AN 2001:301100 Hcaplus, DN 135:76849, Journal of Medicinal Chemistry, (2001), 44(11), 1758-1776.*
Corbett, T. H., "Preclinical Antitumor Efficacy of Analogs of XK469: Sodium-(2-[4-(7-Chloro-2-Quinoxalinyloxy)Phenoxy]Propionate", Investigational New Drugs, 16. (1998),129-139.
Hazeldine, Stuart T., "J. Med. Chem., 2002, 45", *ll. Synthesis and Biological Evaluation of Some Bioisosteres and Congeners of the Antitumor Agent, 2-{4-(7-Chloro-2-quinoxalinyl)oxylphenoxy}propionic Acid (XK469)*, (2002),3130-3137.
Tietze, L. F., et al., "Improved Synthesis of (E)-3-Alkoxy- and (E)-3- Phenoxyacryloyl Chlorides", *Synthesis*, (Nov. 1993), 1079-1080.

* cited by examiner

*Primary Examiner*—Sabiha N. Qazi
(74) *Attorney, Agent, or Firm*—Schwegman, Lundberg, Woessner & Kluth, P.A.

(57) ABSTRACT

The invention provides compounds of the formula:

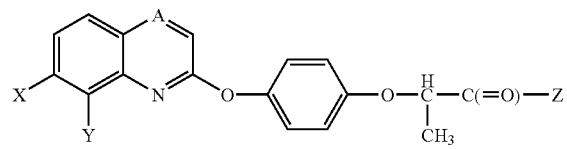

wherein A, X, Y, and Z are as defined in the specification. The compounds are effective anti-tumor agents. The invention also provides pharmaceutical compositions comprising a compound of the above formula or a salt thereof, intermediates useful for preparing a compound of the above formula, and therapeutic methods comprising administering a compound of the above formula or a salt thereof to a mammal in need thereof.

40 Claims, No Drawings

THERAPEUTIC AMIDES

CROSS-REFERENCE TO RELATED APPLICATION

This application claims priority from U.S. Provisional Patent Application No. 60/393,858, filed, Jul. 3, 2002, which is incorporated herein by reference.

GOVERNMENT FUNDING

The invention described herein was made in part with government support under NCI-NIH Grant Number CA82341 awarded by the National Cancer Institute. The United States Government has certain rights in the invention.

BACKGROUND OF THE INVENTION

U.S. Pat. Nos. 5,364,831, and 6,197,728, disclose herbicidal compounds of the formula:

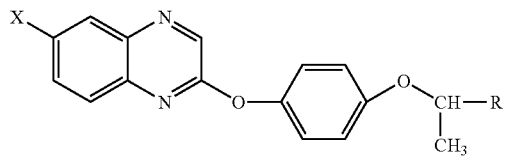

wherein X represents a halogen atom; R includes —C(=O)R$^1$ where R$^1$ represents various substituted alkoxy radicals, —SR$^3$ radicals, and —NHR$^4$ radicals where R$^4$ is a C$_{1-4}$ alkoxycarbonylalkyl, hydroxy alkyl, phenyl, C$_{1-4}$ alkoxy alkyl or di C$_{1-4}$ alkyl amino groups.

U.S. Pat. No. 4,629,493, discloses herbicidal compounds of the formula:

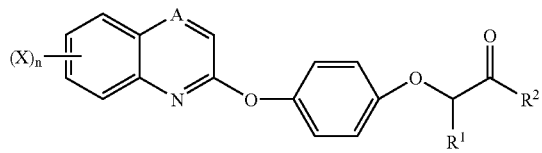

wherein A is —CH— or —N—; X is a halogen; n is 0, 1, or 2; R$^1$ is hydrogen or a lower alkyl group; and R$^2$ is —OH, —Oalkyl, —OM (inorganic or organic salt), —NR$^3$R$^4$ where R$^3$ and R$^4$ respectively represent a hydrogen atom or a lower alkyl group. One of these compounds is currently sold commercially for the control of annual and perennial grass weeds in broadleaf crops. This compound has the following formula:

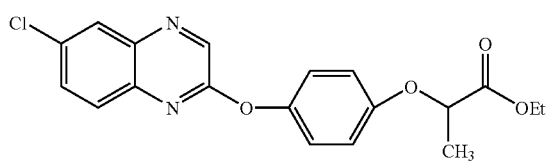

Corbett et. al., *Investigational New Drugs*, 16, 129–139 (1998), evaluated a series of quinoxaline compounds for activity against solid tumors in mice. The following compound

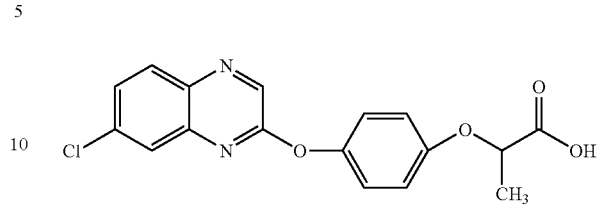

(herein after referred to as XK469) was reported to have broad activity against transplantable mouse tumors. The compound was also reported to have a relatively low potency, and to produce several undesirable side effects, including in vivo toxicity, e.g., paralytic ileus, GI-epithelial damage, marrow toxicity, neuromuscular toxicity, and weight loss.

Hazeldine et al., *J. Med. Chem.*, 2001, 44, 1758–1776, disclose anti-tumor compounds of the formula:

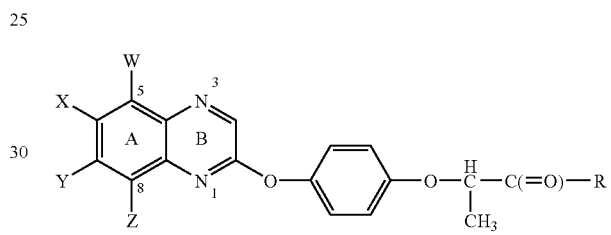

wherein, for example, W can be H or Cl; X can be H, Cl, F, or NO$_2$; Y can be H, F, Cl, Br, I, methoxy or —N$_3$; Z can be H, Cl, or methoxy; and R can be OH, alkoxy, or NR'R", where R' and R" are H, methyl, NH$_2$ or OH, see Table 5 therein.

Hazeldine et al., *J. Med. Chem.*, 2002, 45, 3130, disclose bioisostere and cogener compounds of anti-tumor compound (XK469).

provisional application U.S. Ser. No. 60/309,144, filed Jul. 7, 2001, now PCT application PCT/US02/24442, entitled "Anti-tumor Agents" discloses a compound of the formula:

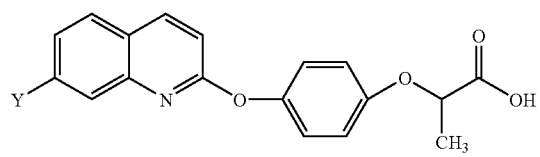

wherein Y is F, Cl, Br, methyl, or methoxy; or a pharmaceutically acceptable salt thereof.

There is currently a need for additional anti-tumor agents.

SUMMARY OF THE INVENTION

The present invention provides compounds that are effective anti-tumor agents. Accordingly, compounds of the invention are of the formula (I):

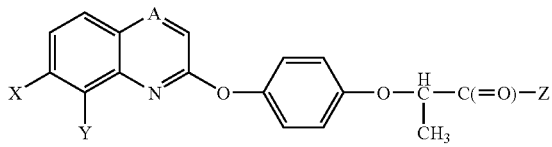

(I)

wherein
A is CH or N;
X is F, Cl, or Br;
Y is hydrogen, hydroxy, or (C$_1$–C$_7$)alkoxy; and
Z is an amino acid, or heterocycle;

or a pharmaceutically acceptable salt thereof.

In some embodiments, there are also provided compounds of the invention which are compounds of the above formula (I):

wherein
A is CH;
X is F, Cl, or Br;
Y is hydroxy, or (C$_1$–C$_7$)alkoxy; and
Z is an —NR$_a$R$_b$;

where R$_a$ and R$_b$ are independently hydrogen, (C$_1$–C$_7$)alkyl, (C$_1$–C$_7$)alkanoyl, aryl, aryl(C$_1$–C$_7$)alkyl, or where R$_a$ and R$_b$ together with the nitrogen to which they are attached are a pyrrolidino, piperidino, morpholino, 1,3-benzodiazepino, 1,4-benzodiazepino, or 1,5-benzodiazepino;

or a pharmaceutically acceptable salt thereof.

In some embodiments, there are also provided compounds of the invention which are compounds of the above formula (I):

wherein
A is CH;
X is F, Cl, or Br;
Y is hydrogen, hydroxy, or (C$_1$–C$_7$)alkoxy; and
Z is —NR$_a$R$_b$;
where R$_a$ and R$_b$ are independently (C$_1$–C$_7$)alkanoyl, aryl, aryl(C$_1$–C$_7$)alkyl, or where R$_a$ and R$_b$ together with the nitrogen to which they are attached are a pyrrolidino, piperidino, morpholino, 1,3-benzodiazepino, 1,4-benzodiazepino, or 1,5-benzodiazepino;

or a pharmaceutically acceptable salt thereof.

In some embodiments, there are also provided compounds of the invention which are compounds of the above formula (I):

wherein
A is N;
X is F, Cl, or Br;
Y is hydroxy; and
Z is an —NR$_a$R$_b$;
where R$_a$ and R$_b$ are independently hydrogen, (C$_1$–C$_7$) alkyl, (C$_1$–C$_7$)alkanoyl, aryl, aryl(C$_1$–C$_7$)alkyl, or where R$_a$ and R$_b$ together with the nitrogen to which they are attached are a pyrrolidino, piperidino, morpholino, 1,3-benzodiazepino, 1,4-benzodiazepino, or 1,5-benzodiazepino;

or a pharmaceutically acceptable salt thereof.

In some embodiments, there are also provided compounds of the invention which are compounds of the above formula (I):

wherein
A is N;
X is F, Cl, or Br;
Y is hydrogen, hydroxy, or (C$_1$–C$_7$)alkoxy; and
Z is —NR$_a$R$_b$;

where R$_a$ and R$_b$ are independently (C$_1$–C$_7$)alkanoyl, aryl, aryl(C$_1$–C$_7$)alkyl, or where R$_a$ and R$_b$ together with the nitrogen to which they are attached are a pyrrolidino, piperidino, morpholino, 1,3-benzodiazepino, 1,4-benzodiazepino, or 1,5-benzodiazepino;

or a pharmaceutically acceptable salt thereof.

The invention also provides a therapeutic method to inhibit tumor cell growth in a mammal, comprising administering to a mammal in need of such therapy, an effective amount of a compound of the invention.

The invention also provides a therapeutic method to treat cancer in a mammal, comprising administering to a mammal in need of such therapy, an effective amount of a compound of the invention.

The invention also provides a therapeutic method to treat cancer in a mammal, comprising co-administering to a mammal in need of such therapy, an effective amount of a mixture of two or more compounds of the invention, for example, a precursor compound of the formula (I).

The invention also provides the use of a compound of the invention in medical therapy.

The invention also provides the use of a compound of the invention to manufacture a medicament for the treatment of cancer in a mammal.

DETAILED DESCRIPTION OF THE INVENTION

Applicants have discovered that compounds of the invention of the formula (I), and in vivo metabolized products of precursor compounds of the invention of the formula (I), administered alone or in combination, can be useful as anti-cancer agents, and for the treatment of cancer.

The following definitions are used, unless otherwise described: halo is fluoro, chloro, bromo, or iodo. Alkyl, alkoxy, etc. denote both straight and branched groups; but reference to an individual radical such as "propyl" embraces only the straight chain radical, a branched chain isomer such as "isopropyl" being specifically referred to. When alkyl can be partially unsaturated, the alkyl chain may comprise one or more (e.g. 1, 2, 3, or 4) double or triple bonds in the chain.

"Aryl" denotes a phenyl radical or an ortho-fused bicyclic carbocyclic radical having about nine to ten ring atoms in which at least one ring is aromatic.

"Arylalkyl" or "aryl(C$_1$–C$_7$)alkyl" refer to a group of the formula aryl(C$_1$–C$_7$)alkyl-, where aryl and (C$_1$–C$_7$)alkyl are as defined herein.

The term "amino acid," comprises the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. taurine, phosphoserine, phosphothreonine, phosphotyrosine, hydroxyproline, gamma-carboxyglutamate, hippuric acid, octahydroindole-2-carboxylic acid, statine, 1,2,3,4,-tetrahydroisoquinoline-3–carboxylic acid, penicillamine, ornithine, citruline, α-methyl-alanine, para-benzoylphenylalanine, phenylglycine, propargylglycine, sarcosine, and tert-butylglycine). The term also comprises natural and unnatural amino acids bearing a conventional amino protecting group (e.g. acetyl or benzyloxycarbonyl), as well as natural and unnatural amino acids protected at the carboxy terminus (e.g. as a $(C_1-C_7)$alkyl, phenyl or benzyl ester or amide; or as an α-methylbenzyl amide). Other suitable amino and carboxy protecting groups are known to those skilled in the art (See for example, T. W. Greene, *Protecting Groups In Organic Synthesis*; Wiley: New York, 1981, and references cited therein). An amino acid can be linked to the remainder of a compound of formula (I) through the carboxy terminus, the amino terminus, or through any other convenient point of attachment, such as, for example, through the sulfur of cysteine. A particularly preferred amino acid is taurine ($H_2N-(CH_2)_2-SO_3H$), or salts thereof, which is covalently bonded at its N-terminus to the carbonyl of the compound of formula (I).

"Heterocycle" encompasses a Z radical attached or linked to the carbonyl carbon via a nitrogen ring atom of a monocyclic, fused-bicyclic, or bridged-bicyclic, saturated or unsaturated, ring system containing five or twelve ring atoms consisting of carbon and one to four heteroatoms each selected from the group consisting of non-peroxide oxygen, sulfur, and at least one N(X) wherein X is absent or is H, O, $(C_1-C_4)$alkyl, phenyl or benzyl. Preferred heterocycles can be, for example, pyrrolidino, piperidino, morpholino, 1,3-benzodiazepino, 1,4-benzodiazepino, or 1,5-benzodiazepino.

An "isolated" compound refers to a compound that is separated from the environment in which it may be normally present. For example, a compound may be separated from nature to produce an isolated compound.

"Partially unsaturated" means, for example, a $(C_1-C_7)$ alkyl which is optionally partially unsaturated, means the named substituent has one or more unsaturations, such as one or more double bonds, one or more triple bonds, or both.

A "purified" compound refers to a compound that is present in a given quantity at a concentration of at least 50%, 60%, 70%, 80%, 90% and intermediate values thereof. For example, an isolated compound may be present at 51%, 52%, 53%, 54% and the like. Preferably the compound is present at 90% to 95% and intermediate values thereof. More preferably the compound is present at 95% to 99%, and intermediate values thereof. Even more preferably the compound is present at 99% to 99.9% and intermediate values thereof. Most preferably the compound is present at greater than 99.9% of a given quantity.

"Optional" or "optionally" mean that the subsequently described event or condition may but need not occur, and that the description includes instances where the event or condition occurs and instances in which it does not. For example, "optionally substituted" means that the named substituent may be present but need not be present, and the description includes situations where the named substituent is included and situations where the named substituent is not included.

The terms "include", "for example", "such as", and the like are used illustratively and are not intended to limit the present invention.

The indefinite articles "a" and "an" mean "at least one" or "one or more" when used in this application, including the claims, unless specifically indicated otherwise.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine, for example, anti-tumor activity, herbicidal activity, or other therapeutic activity using the standard tests described herein, or using other similar tests which are well known in the art.

Specific and preferred values listed below for radicals, substituents, and ranges, are for illustration only; they do not exclude other defined values or other values within defined ranges for the radicals and substituents. The compounds of the invention include compounds of formula (I) having any combination of the values, specific values, more specific values, and preferred values described herein.

Specifically, $(C_1-C_7)$alkyl can be methyl, ethyl, propyl, isopropyl, butyl, iso-butyl, sec-butyl, pentyl, 3-pentyl, hexyl, or heptyl; $(C_1-C_7)$alkoxy can be methoxy, ethoxy, propoxy, isopropoxy, butoxy, iso-butoxy, sec-butoxy, pentoxy, 3-pentoxy, hexyloxy, 1-methylhexyloxy, or heptyloxy; $(C_1-C_7)$alkanoyl can be acetyl, propanoyl, butanoyl, pentanoyl, 4-methylpentanoyl, hexanoyl, or heptanoyl; aryl can be phenyl, indenyl, or naphthyl.

When $(C_1-C_7)$alkyl is unsaturated or partially unsaturated, it can specifically be vinyl, allyl, 1-propenyl, 2-propenyl, 1-butenyl, 2-butenyl, 3-butenyl, 1,3-butadienyl, 1-pentenyl, 2-pentenyl, 3-pentenyl, 4-pentenyl, 1-hexenyl, 2-hexenyl, 3-hexenyl, 4-hexenyl, 5-hexenyl, ethynyl, 1-propynyl, 2-propynyl, 1-butynyl, 2-butynyl, 3-butynyl, 1-pentynyl, 2-pentynyl, 3-pentynyl, 4-pentynyl, 5-hexene-1-ynyl, 2-hexynyl, 3-hexynyl, 4-hexynyl, or 5-hexynyl.

A specific value for X is F, Cl, or Br.

Another specific value for X is Cl.

Another specific value for X is Br.

A specific value for Y is hydrogen, hydroxy, or $(C_1-C_7)$alkoxy.

Another specific value for Y is hydrogen (—H).

Another specific value for Y is hydroxy (—OH).

Another specific value for Y is $(C_1-C_7)$alkoxy.

Another specific value for Y is methoxy (—OMe).

A specific value for X is Z is —$NR_aR_b$.

Another specific value for Z is —$NH_2$.

Another specific value for Z is —$NHCH_3$.

Another specific value for Z is —$N(CH_3)_2$.

Another specific value for Z is pyrrolidino.

Another specific value for Z is piperidino.

Another specific value for Z is morpholino.

Another specific value for Z is 1,3-benzodiazepino.

Another specific value for Z is 1,4-benzodiazepino.

Another specific value for Z is 1,5-benzodiazepino.

Another specific value for Z is an amino acid.

Another specific value for Z is an alpha-amino acid.

Another specific value for Z is an amino acid having an alpha-carbon atom having a non-hydrogen substituent in the (L) configuration.

Another specific value for Z is an amino acid having an alpha-carbon atom having a non-hydrogen substituent in the (D) configuration.

Another specific value for Z is —$NH-(CH_2)_2-SO_3H$.

Another specific value for Z is —$NH-CH_2-CO_2H$.

Another specific value for Z is —$NH-CH(CH_3)-CO_2H$.

A specific group of compounds of Formula (I) are compounds wherein the carbon bearing the methyl group is in the (D) configuration.

A preferred group of compounds of Formula (I) are compounds wherein the carbon bearing the methyl group is in the (L) configuration.

Preferred compounds of the invention are, for example:
2-{4-((7-Bromo-2-quinolinyl)oxy) phenoxy}propionmethylamide;
2-{4-((7-Chloro-2-quinolinyl)oxy) phenoxy}propiondimethylamide;
(2-(4-(7-Chloro-2-quinoxalinyl)oxy)phenoxy)propionylamino ethanesulfonic acid;
(2-(4-(7-Bromo-2-quinolinyl)oxy)phenoxy)propionylamino ethanesulfonic acid;
{2-{4-(7-Bromo-quinolin-2-yloxy) phenoxy}propionylamino}acetic acid;
{2-{4-(7-Chloro-quinoxalin-2-yloxy)-phenoxy}propionyl amino}acetic acid;
(R)(2-(4-(7-Bromo-2-quinolinyl)oxy)phenoxy)propionylamino ethanesulfonic acid;
(R){2-[4-(7-Bromo-quinolin-2-yloxy)-phenoxy]-propionylamino}acetic acid; and
(R){2-{4-(7-Chloro-quinoxalin-2-yloxy)-phenoxy}propionyl amino}acetic acid;
or pharmaceutically acceptable salts thereof.

Preferred compounds of the invention are, for example, of formula:

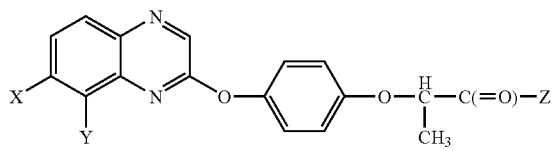

where X is Cl, Y is hydrogen or (C$_1$–C$_7$)alkoxy, and Z is —NR$_a$R$_b$, or an amino acid; and compounds of the invention of the formula:

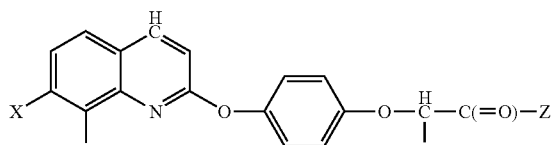

where X is Cl or Br, Y is hydrogen or (C$_1$–C$_7$)alkoxy, and Z is —NR$_a$R$_b$, or an amino acid; or pharmaceutically acceptable salts thereof.

More preferably, the compounds of the invention are of the formula:

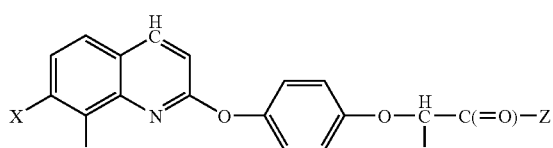

where X is Cl or Br, Y is hydrogen or methoxy, and Z is an amino acid; or pharmaceutically acceptable salts thereof.

Still more preferably, the compounds of the invention are of the formula:

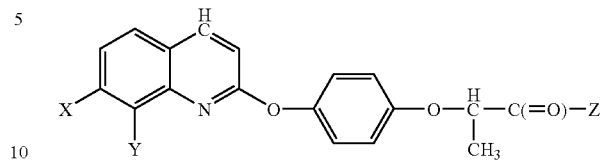

where X is Cl or Br, Y is hydrogen or methoxy, Z is an amino acid of the corresponding (R) enantiomer(s); or pharmaceutically acceptable salts thereof.

The invention also provides a therapeutic method to treat cancer in a mammal, comprising administering to a mammal in need of such therapy, an effective amount of a compound of the invention, for example, a compound of the formula (I) wherein Z is taurine or glycine. Another treatment method of the present invention includes co-administration of different compounds of the invention of the formula (I), for example, a mixture of two or more compounds of formula (I).

In cases where compounds are sufficiently basic or acidic to form stable non-toxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (e.g., sodium, potassium or lithium) or alkaline earth metal (e.g., calcium) salts of carboxylic acids can also be made.

The compounds of Formula (I) can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, dimethyl sulfoxide (DMSO), alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of Formula (I) to the skin are known to the art; for example, see Jacquet et al. (U.S. Pat. No. 4,608,392), Geria (U.S. Pat. No. 4,992,478), Smith et al. (U.S. Pat. No. 4,559,157), and Wortzman (U.S. Pat. No. 4,820,508).

Useful dosages of the compounds of Formula (I) can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The compound is conveniently administered in unit dosage form; for example, containing 5 to 1,000 mg/m$^2$, conveniently 10 to 750 mg/m$^2$, most conveniently, 50 to 500 mg/m$^2$ of active ingredient per unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The compounds of the invention are effective anti-tumor agents and have higher potency and/or reduced toxicity as compared to XK469. Preferably, compounds of the invention are more potent and less toxic than XK469 (R), and/or avoid a potential site of catabolic metabolism encountered with XK469, i.e., have a different metabolic profile than XK469.

The present invention provides therapeutic methods of treating cancer in a mammal, which involve administering to a mammal having cancer an effective amount of a compound or a composition of the invention. A mammal includes a primate, human, rodent, canine, feline, bovine, ovine, equine, porcine, caprine, and the like. Cancer refers to any various type of malignant neoplasm, for example, colon cancer, breast cancer, melanoma and leukemia, and in general is characterized by an undesirable cellular proliferation, e.g., unregulated growth, lack of differentiation, local tissue invasion, and metastasis.

The ability of a compound of the invention to treat cancer may be determined by using assays well known to the art.

For example, the design of treatment protocols, toxicity evaluation, data analysis, quantification of tumor cell kill, and the biological significance of the use of transplantable tumors screens are documented. In addition, ability of a compound to treat cancer may be determined using the Tests as described below.

The following general methodologies were employed in evaluating compounds of the invention and known anti-cancer compounds:

Tumor and Animal Maintenance

Pancreatic ductal adenocarcinoma-03, mammary adenocarcinoma-16/C, mammary adenocarcinoma-17/Adr, and human melanoma LOX were used in the studies. Tumors were maintained in the mouse strain of origin (C57B1/6 for Panc-03 and $C_3H$ for the mammary tumors). Balb/c SCID mice (B and T cell deficient) were used for tumor maintenance and chemotherapy trials involving the human melanoma LOX. Tumors were transplanted into the appropriate $F_1$ hybrid (B6D2F1=C57B 1/6 female× DBA/2 male) or the strain of origin for the chemotherapy trials. Individual mouse body weights for each experiment were within 5 grams, and all mice were over 17 grams at the start of therapy. The mice were supplied food and water ad libitum.

Chemotherapy of Solid Tumors

Animals were pooled, implanted subcutaneously with 30 to 60 mg tumor fragments by a 12 gauge trocar on day 0, and again pooled before unselective distribution to the various treatment and control groups. For early stage treatment, chemotherapy was started within 1 to 3 days after tumor implantation while the number of cells was relatively small ($10^7$ to $10^8$ cells). For upstaged or advanced staged trials, the tumors were allowed to grow for five or more days before treatment was started. Tumors were measured with a caliper twice weekly. Mice were sacrificed when their tumors reached 1,500 mg. Tumor weights are estimated from two-dimensional measurements:

Tumor weight (in mg)=$(a \times b^2)/2$, where a and b are the tumor length and width in (mm), respectively.

End Points for Assessing Anti-Tumor Activity for Solid Tumors

The following quantitative endpoints were used to assess anti-tumor activity:

a) Tumor growth delay (T–C value), where T is the median time (in days) required for the treatment group tumors to reach a predetermined size (e.g., 1,000 mg), and C is the median time (in days) for the control group tumors to reach the same size. Tumor-free survivors were are excluded from these calculations (cures are tabulated separately). This value is an important criterion of anti-tumor effectiveness because it allows the quantification of tumor cell kill.

b) Calculation of tumor cell kill for subcutaneously (SC) growing tumors. The $log_{10}$ cell kill was calculated from the following formula:

$$Log_{10} \text{ cell kill total (gross)} = (T-C \text{ value in days})/(3.32)(Td)$$

where T–C is the tumor growth delay as described above and Td is the tumor volume doubling time (in days), estimated from the best fit straight line from a log-linear growth plot of the control group tumors in exponential growth (100 to 800 mg range). The conversion of the T–C values to $log_{10}$ cell kill is possible because the Td of tumors re-growing post treatment (Rx) approximates the Td values of the tumors in untreated control mice.

In selected cases, both for historic in vivo evaluation data as well as data presented here, it is of value to compare log kill numbers from trials of markedly different testing schedules. For this purpose, an activity table was created, and is presented below. It should be noted that an activity rating of +++ to ++++ is needed to effect partial regression (PR) or complete regression (CR) of 100 to 300 mg size masses of most transplanted solid tumors of mice. Thus, an activity rating of + or ++ would not be scored as active by usual clinical criteria. A PR is a reduction in tumor mass to less than 50% of pretreatment size. A CR is a reduction in tumor mass to below palpable size (i.e., reduction to zero detectable mass).

| Conversion of $log_{10}$ tumor cell kill to an activity rating | |
|---|---|
| Anti-tumor activity | Duration of Rx 5 to 20 days $log_{10}$ kill (gross) |
| Highly active ++++ | >2.8 |
| +++ | 2.0–2.8 |
| ++ | 1.3–1.9 |
| + | 0.7–1.2 |
| – | <0.7 |

The treatment and control groups were measured when the control group tumors reach approximately 700 to 1,200 mg in size (median of group). The T/C value in percent is an indication of anti-tumor effectiveness: A T/C=0% means no tumor growth. A T/C=100% means no anti-tumor activity, i.e., the treated and control tumors grew equally. A T/C equal to or less than 42% is considered significant anti-tumor activity by the Drug Evaluation Branch of the Division of Cancer Treatment (NCI). A T/C value<10% is considered to indicate highly significant anti-tumor activity, and is the level used by NCI to justify a clinical trial if toxicity, formulation, and certain other requirements are met (termed DN-2 level activity). A body weight loss nadir (mean of group) of greater than 20% or greater than 20% drug deaths is considered to indicate an excessively toxic dosage in most single course trials.

Drug Preparation for Injections in Mice

Compounds as their sodium salts were prepared in a 1% sodium bicarbonate solution, $H_2O$ or phosphate buffered saline (PBS), with pH adjusted to 7.0 to 7.5 with HCl, and administered intravenously (IV) or orally (PO), at injection volumes of 0.2 mL per injection.

Amide Compound—In-Vivo Test Data

The following summarizes the results for compounds of the present invention prepared (Table A) and compared (Tables 1–10) with XK469.

Table 1. This data separately compared XK469 and compound 14a against early stage pancreatic adenocarcinoma 03 in $BDF_1$ male mice.

Cage 5: compound 14a was given at 120 mg/kg/inj IV, 1×/day on days 3–6, 9–11 and BID on days 7–8 for a total dose of 1,320 mg/kg. There was a –0.8 g (–3.6%) body weight loss. Toxicity was not reached at this dose. Compound 14a was active, producing a 7.3% T/C and a 1.9 log cell kill (++ activity rating). This was the highest non-toxic dose (HTND).

Cage 6: Compound 14a was given at 60 mg/kg/inj IV, 1×/day on days 3–6, 9–11 and BID on days 7–8 for a total dose of 660 mg/kg. There was a –0.4 g (–1.8%) body weight loss and 0/5 drug deaths. This dose was minimally active, producing a 40% T/C and a 0.7 log cell kill (+ activity rating).

Cage 7: Compound 14a was given at 30 mg/kg IV, 1×/day on days 3–6, 9–11 and BID on days 7–8 for a total dose of 330 mg/kg. There was a 0.4 g (–1.8%) body weight loss and no lethality. This dose was inactive, producing a 74% T/C and a 0.3 log cell kill {(–) inactive activity rating}.

Cage 8: Compound XK469 was given at 60 mg/kg IV on days 3–5 for a total dose of 180 mg/kg. Treatment was stopped early due to scruffy appearance of the mice and a –3.6 g (–15.5%) body weight loss at nadir on day 8. There were no drug deaths and mice recovered their weight on day 13. Historically, the MTD for XK469 is 450–480 mg/kg IV. Nevertheless, this sub-optimal dose of 180 mg/kg was active, producing a T/C=11% and a 1.43 log cell kill (++ activity rating).

Table 2. This data separately compared XK469 and compound 14b against early stage pancreatic ductal adenocarcinoma 03.

Compound 14b, the mono-methylamide of XK469, was evaluated against early stage Pancreatic Ductal Adenocarcinoma 03. Note that the compound was water insoluble and was thus given orally.

Cage 2: XK469 Control: XK469 was injected IV, QD3–6, 10 for a total of 300 mg/kg. This produced a –15% body wt loss; nadir day 8, full recovery day 12 (estimate). This dose was highly active (1/5 cures, 3.3 log kill among those not cured, ++++ activity rating).

Cage 3: 14b was given PO at 150 mg/kg/inj. BID day 3. The dose was increased to 250 mg/kg/inj BID days 4–7 for a total of 2,300 mg/kg. This produced a –9% body wt. loss, nadir day 8 with full recovery on day 10. This dose was modestly active (T/C=39%, 0.8 log kill, + activity rating).

Cage 4 and 5: Treatments were discontinued early to conserve the scarce compound.

Table 3. This data separately compared XK469 and compound 14c against a multi-drug resistant mammary adenocarcinoma (M17/Adr). Compound 14c (the dimethyl amide derivative of 8-methoxy XK469) was active (Cage 5).

Cage 1: No treatment control: Time to 1,000 mg=8.5 days (1.1 day Td). Tumor growth as expected.

Cage 2: (neg control) Adriamycin was given IV at 7.5 mg/kg/inj days 1, 7 for a total of 15 mg/kg. This dose is historically an MTD. It was inactive (T/C=90%).

Cage 4: XK469 was given IV at 56 mg/kg/injection QD-1–5 and 10 for a total of 336 mg/kg. This was nicely active: T/C=9%, 4.2 log kill, ++++ activity rating.

Cage 5: Compound 14c is the dimethylamide of the carboxylic acid compound 13a. Compound 14c was given PO at 145 mg/kg/inj QD-1–3 and 7–9 for a total of 870 mg/kg. Toxicity was not reached. This dose was active (T/C=20%; 1.5 log kill; ++ activity rating. Note the design of this schedule. If adaption to the drug was going to occur, it would occur on this schedule. One would then expect that anti-tumor activity would be markedly reduced (compared to 13a on a short, high dose intensity schedule). Furthermore, one would expect that the next lower dosages would be essentially inactive on this schedule. In actual fact, the activity was not reduced and the next lower dosages were still active. In a short, dose-intense schedule (BID-1–3), 13a (by the IV route) produced a 7% T/C and a 1.5 log kill at 162 mg/kg total dose (exactly the log kill activity found for 14c at 870 mg/kg PO).

Cage 6: 14c was given PO at 90 mg/kg/inj QD-1–3 and 7–9 for a total of 540 mg/kg. This dose was active: T/C=31%; 1.4 log kill, ++ activity rating.

Cage 7: 14c was given PO at 55.8 mg/kg/inj QD-1–3 and 7–9 for a total of 334.8 mg/kg. This dose was active: T/C=31%; 1.0 log kill, + activity rating.

Cage 8: 14c was given PO at 34.6 mg/kg/inj QD-1–3 and 145 mg/kg/inj QD-7–9 for a total of 538.8 mg/kg to match the total dose of cage 6. This dose was modestly active (0.9 log kill, + activity rating). If there was no adaptation to the drug, the log kill should have been the same as Cage 6. The activity was reduced (compared to Cage 6), but the fact that any activity occurred would seem to indicate that there was not much adaptation.

Table 4: This data separately compares XK469 and compound 14e (the dimethyl amide of 11b) against a pancreatic adenocarcinoma (P03). Compound 14e was active (Cage 2) and an improvement over XK469 (Cage 5). The higher dose requirement for compound 14e may be a disadvantage over compound 11b (Cage 14).

This trial was designed to separately evaluate compounds 11b, 14e, and XK469 (R enantiomer).

Cage 1: No treatment control: Time to 1,000 mg=12.5 days (2.0 day Td). This was the fast growing subline of Panc-03. It is less curable than the older slow line. Otherwise, the behavior and growth was as expected.

Cage 2: Compound 14e was given PO at 120 mg/kg/inj 2×/day, days 3–9 for a total of 1680 mg/kg. There was no evident toxicity and the mice gained weight. This dose (although very large) was nicely active (T/C=8.3%, 2.5 log kill, +++ activity rating).

Cage 3: Compound 14e was given PO at 60 mg/kg/inj 2×/day, days 3–9 for a total of 840 mg/kg. This dose was almost as active as the next higher dose. Considering the next lower dose (Cage 4) was almost inactive indicated that the top dose (Cage 2) was poorly absorbed from the GI. This often happens with very large dosages of water insoluble compounds. Again, however, the dose used in Cage3 was very large (840 mg/kg total). Although active (2.2 log kill) it was not superior to compound 11b.

Cage 4: Compound 14e was given PO at 30 mg/kg/inj 2×/day, days 3–9 for a total of 420 mg/kg. This dose was marginally active by T/C but inactive by log kill.

Cage 5: XK469 (R) was given IV at 57 mg/kg/injection, QD 3–9 for a total of 399 mg/kg. This is historically an adequate dose on this schedule. This produced a –6.7% body weight loss, nadir day 8, full recovery day 11. This was active (T/C=4.1%, 1.7 log kill, ++ activity).

Cage 6: XK469 (R) was given IV at 38 mg/kg/injection, QD 3–9 for a total of 266 mg/kg. This was active (T/C=8.3%, 1.4 log kill, ++ activity rating).

Cage 14: Compound 11b (racemic) was given IV at 48 mg/kg/inj QD 3–9 for a total of 336 mg/kg. This produced a –8.9% body weight loss (nadir day 11). Unfortunately the mice were not weighed days 12, 13, 14, 15, 16 and by day 17 were more than a gram per mouse above the pretreatment weight. This considered, it is likely that full weight recovery occurred around day 15. This dose was active (T/C=0%, 2.6 log kill, +++ activity rating). This was more active than XK469 and modestly more active than compound 14e. Note that compound 11b has a lower dose requirement than XK469.

Table 5. This data separately compares XK469 (R) and racemic compound 14f against a pancreatic adenocarcinoma (P03). Compound 14f (Cage 3) had activity similar to that of XK469 (R) (Cage 2). Thus, compound 14f was well tolerated at the dose given and produced no weight loss or other adverse symptoms. However, toxicity was not reached, and the higher dose requirement is a reflection of the racemic mix tested in this experiment being half-inert as the "S" form was found to be inactive (see Table 6 below).

Cage 2: XK469 (R) was injected IV once daily at 45 mg/kg/inj days 3 through 10 for a total dose of 360 mg/kg. A 7% body weight loss nadir occurred d11 with full recovery by d14. This dose was active, producing a T/C of 21% and a log cell kill of 1.84 (++ activity rating).

Cage 3: Compound 14f was injected IV days 3–8 with the following doses: 60 mg/kg/inj (once daily, d3–5, bid d6) 80 mg/kg (bid d7, once daily d8). The route was then switched (for some of the mice) to SC due to tail vein damage. The remainder of the treatment was as follows: 80 mg/kg/inj (once daily SC d9–11, with 3 mice being injected IV on d11). The final total dose was 780 mg/kg. There was no weight loss observed. This dose was as active (T/C=10%, log cell kill=1.67, ++ activity rating).

Table 6. This data separately compares XK469 (R) and each of the "R" and "S" enantiomers of compound 14f against a human melanoma (LOX) in SCID mice. The "S" enantiomer of compound 14f was inactive (Cage 3) and had no toxicity associated with it other than a mild transient agitation on the last day of injection. Compound 14f (R) (Cage 2) is the active form, with activity comparable to that of XK469 (R) (Cage 4). The "R" form produced some toxicity: weight loss (−13.5%) and white paws (indicative of leukopenia) which resolved within 4 days of onset. However, what is most interesting is that both compound 14f enantiomers were better tolerated than expected. It is also instructive to compare the total respective doses of XK469 and compound 14f given in Table 5 with this trial. Note that the SCID mice tolerated a comparatively higher dose of compound 14f than XK469. Historically, SCID mice tolerate approximately 40–50% of the conventional mouse maximum tolerated dose (MTD) of XK469.

Cage 2: Compound 14f (R) was injected IV, QD1–6, BID on day 7 for a total dose of 700 mg/kg. There was minimal anti-tumor activity at this dose (T/C=47%, log kill=0.8). There was a −2.8 g weight loss (−13.5%; nadir day 13) and no drug deaths. On day 14, the mice were noted as having white paws (indicative of leukopenia). These symptoms resolved by day 18.

Cage 3: Compound 14f (S) was injected IV, QD1–6, BID on day 7 for a total dose of 700 mg/kg. There was minimal anti-tumor activity at this dose (T/C=71%, log kill=0.3). The symptoms associated with the "R" enantiomer (see above) did not manifest with the "S" form of the drug. Mice treated with the "S" enantiomer gained weight during the course of treatment (+2.0% on day 8), and exhibited mild agitation/ hyperactive behavior on the last day of treatment.

XK469 (R) was injected IV, QD1–7 for a total dose of 175 mg/kg. There was anti-tumor activity at this dose (T/C=34%, log kill 0.8). Historically, SCID mice tolerate approximately 50% of the conventional mouse MTD (360 mg/kg).

Table 7. This data separately compares Compound 14g Racemic, Compound XK469 (R), and 2-{4-{(7-bromo-2-quinolinyl)oxy}phenoxy}propionic acid compound 11c (R) against Early Stage Mammary Adenocarcinoma 16/C. An extended injection schedule (Q2d×7) may have yielded a better comparison by avoiding the excessive weight loss. This evaluation was repeated on an extended injection schedule with the "R" form of compound 14g and confirmed its enantiomeric activity and was compared with compounds 11c (R), see Table 9 below. Nonetheless, compound 14g racemic was active, producing ⅕ (20 percent) tumor free animals (day 161). The animal was then re-implanted with Mam16/C/71. The tumor implants grew successfully, indicating no immunologic factors were involved with the original cure. Note that compound 14g racemic was tolerated at twice the dose (moderate weight loss of −11%), indicating that either the "R" or the "S" enantiomer is inert, as was the case with 14f, the taurine derivative of XK469.

Compound 14g Racemic: The compound was injected twice daily at 60 mg/kg IV, days 1–5 with a four hour split between injections. Injections were stopped due to tail vein damage. There was an 11% weight loss (nadir day 4) with full recovery by day 10 (6 day host recovery time). This course of treatment was active (T/C=14%, log cell kill=0.9, + activity rating). One animal remained tumor free to day 161. The animal was then re-implanted with Mam16/C/71 to verify that it was a cure. The tumor implants grew successfully, indicating no immunologic factors were involved with the original cure.

Compound XK469 (R): The compound was injected with 50 mg/kg/inj IV days 1–5 for a total dose of 250 mg/kg. Injections were stopped due to weight loss and poor physical appearance (−15.3% body weight loss day 6 with scruffy appearance). The animals developed diarrhea (noted day 7) and the weights continued to drop (body weight loss nadir of −21.2% occurred day 7). The mice began to recover weights day 8 and had regained pre-injection weight by day 12. Although there were no lethalities, this dose would be considered toxic due to the excessive weight loss (>20%). The $C_3H$ strain is not exceptionally hardy, as the usual MTD is in the 360–450 mg/kg range. Nonetheless, XK469 was active (T/C=4%, log cell kill=1.6, ++ activity rating).

Compound 11c (R): This compound was given at 48 mg/kg/inj IV qd 1–5 for a total dose of 240 mg/kg. Injections were stopped due to weight loss and poor physical appearance (−17.5% body weight loss day 6 and a ruffled appearance). The animals continued to drop weight and diarrhea was noted in some of the animals days 8 and 9. One animal died day 10, with the necropsy report confirming a drug death (diarrhea at death with a soft GI and a small liver and spleen). This dose would also have to be considered toxic due to the excessive weight loss noted at the nadir (−29.4% on day 9), though the surviving animals did recover to pre-injection weight by day 13. 11c was active at this toxic dose (0% T/C, log cell kill=1.8, ++ activity rating).

Other compounds were evaluated in vivo as discussed below and as summarized in Tables 8–10.

Table 8. The "R" enantiomers of compound 11c, compound XK469, and compound 14f were separately evaluated on an extended schedule against early stage murine mammary adenocarcinoma 16/C. This trial confirms the activity of the "R" moiety of 14f. Note the similarities in activity for 11c (R) (Cage 2), XK469(R) (Cage 3), and 14f (R) (Cage 4), except for the higher dose requirement of 14f. The "R" enantiomers were essentially equivalent in activity, producing >4.0 log cell kill (++++ activity rating) on the extended, intermittent injection schedule. All three agents were well tolerated with moderate body weight loss noted for XK469 (−7.4%). 14f and 11c (R) produced more modest weight loss (−3.0% and −4.3% respectively). In keeping with the rapid host recovery times of this series, all weight loss was fully recovered within 2–4 days of nadir.

11c (R): Cage 2 was injected with 60 mg/kg/inj every other day, starting on day 1 for a total dose of 480 mg/kg. On this extended schedule, 11c (R) was well tolerated and no adverse effects were noted. There was modest weight loss of −1.14 g (−4.3%); the nadir occurred on d14, with full recovery by d17. This dose was highly active (0% T/C, 4.8 log cell kill, activity rating:++++) but there were no cures.

XK469 (R): Cage 3 was injected with 60 mg/kg/inj on a Q2d×8 schedule starting on day 1 for a total dose of 480 mg/kg. On this extended schedule XK469 (R) was also well tolerated, producing a body weight loss of −2.0 g (7.4%); the nadir occurred d17, with full weight recovery by d20. XK469 (R) was highly active on this schedule (T/C=0%, log cell kill=5.4, ++++ activity rating). There were no cures.

14f (R): Cage 4 was injected with the following escalation of doses: 80 mg/kg/inj (d1), 100 mg/kg (d3), 120 mg/kg (d4), 160 mg/kg (d5), 200 mg/kg (d7, 9) and 250 mg/kg (d11, 13, 15) for a total dose of 1610 mg/kg. 14f (R) was well tolerated on this dose/schedule producing a modest weight loss of −0.8 g (−3.0%). Weight loss nadir occurred on d14, with full recovery by day 16. The "R" enantiomer of 14f was highly active (T/C=0%, log cell kill=4.2, ++++ activity). There were no adverse symptoms noted post injection of compound 14f (R) and no cures.

Cage 5 was injected with the following escalation of doses: 50 mg/kg/inj (d1), 65 mg/kg (d3), 75 mg/kg (d4), 100 mg/kg (d5) and 125 mg/kg (d6, 7, 9,) for a total dose of 665 mg/kg. Injections were stopped at this point to conserve drug supplies. This lower dose of 14f (R) was also active (14% T/C, 1.8 log cell kill, ++ activity rating).

Table 9. This evaluation confirmed the activity of the "R" enantiomer of compound 14g. The lower limit of solubility for 14g (R) precluded an evaluation of this compound by the IV route, so IP injections were given instead. With the exception of a higher dose requirement for 14g (R), the compound was equivalent in efficacy (Cage 3, ++ activity rating) to that of the parent, 11c (R) (Cage 5, ++ activity rating) by this route and short intense schedule of administration.

The "R" enantiomers of 14g and 11c were given IP on a daily schedule against early stage Pancreatic Adenocarcinoma 03. The IP route was used for two reasons. First, the "R" form of 14g has a solubility limit of 25 mg/kg (0.2 ml/inj). This is approximately 40% of the dose given IV with the racemic mix (60 mg/kg, see Table 7). The "R" form's low solubility made IV injection a technically unsuitable route of administration due to an excessive number of injections required to deliver an adequate total dose. Second, although this drug series is just as active orally, the PO route was not used for this trial because of the possibility that the amide bond would be subject to cleavage by the strong acids present in the stomach. For this same reason, 14g (R) was prepared without acid or base to minimize any possibility of cleavage regenerating the parent compound (11c (R)).

14g (R): Cage 2 was injected IP with 75 mg/kg/inj BID (2×/day) on days 3–5 for a total dose of 450 mg/kg. The animals were noted as having increased urinary output and a sunken appearance, indicating possible diuretic effect from the drug. The dose was toxic, with one drug death occurring day 10. Necropsy results indicated a normal size stomach and liquid filled upper and lower GI (diarrhea). A mean body weight loss of 23.4% occurred day 9, with the remaining surviving animals recovering to pre-injection weight by day 17. Although this dose was toxic, 14g (R) was active (T/C=0%, log cell kill=1.52, ++ activity rating). In hindsight, an extended every other day injection schedule would be better tolerated.

Cage 3 was injected IP with 45 mg/kg/inj BID on days 3–7 for a total dose of 450 mg/kg. Injections were stopped as these animals were also exhibiting signs of diuretic effect. The mean body weight loss of 6.7% occurred d9, with full weight recovery by d12. This dose was active on this schedule, producing a T/C=12.6%, log cell kill=1.72, ++ activity rating.

11c (R): Cage 4 was injected IP with the following doses: 50 mg/kg/inj days 3–5, 7 and 60 mg/kg/inj. day 6 for a total dose of 260 mg/kg. Injections were stopped due to onset of weight loss (nadir of −16.7% with full recovery by day 17) and poor appearance (scruffy, hunched, high urinary output). One drug death occurred on d 11. Necropsy results indicated normal spleen, liquid filled GI (upper and lower) and pale paws. In hindsight, an extended every other day schedule would have been better tolerated.

Cage 5 was injected with 30 mg/kg/inj (days 3–5,7) and 37.5 mg/kg/inj (day 6) for a total dose of 157.5 mg/kg. This dose produced no weight loss or external signs of distress. The dose was active (T/C=26%, log cell kill=1.58, ++ activity rating).

Table 10. The R enantiomers of 14h (R), 14i (R), 11c (R) and XK469 (R) were evaluated on extended injection schedules against early stage pancreatic adenocarcinoma 03. Low water solubility limits encountered with 14h (R) (this trial) and 14g (R) previously (see Table 9), precluded IV administration for technical reasons (too many injections). The oral (PO) route, which is the preferred alternate route for this drug series, was deemed not feasible due to potential cleavage of the amide bonds of 14h and 14i (R) by the low pH environment present in the stomach. Thus, for this test, all compounds initially were to be given IP, in an attempt to identify a suitable alternate route of administration. However, sustained pain production was noted after the first IP injection of 14i (R). As this compound retained good water solubility, the route was switched to IV for subsequent injections (Cage 4). At a total dose of 455 mg/kg, given on an extended schedule, 14i (R) produced a 10% T/C, 1.6 log kill (++ activity rating) confirming activity of the R form of the compound. Considering the modest weight loss, it is likely that higher dosages could have been administered (with likely greater efficacy). However, 14i (R) does require a higher total dose than the parent compound, XK469 (R). In Cage 7, XK469 (R) at 350 mg/kg total dose, given IP on the same schedule produced a 5% T/C, a 2.2 log kill, for a +++ activity rating.

14h (R): given IP also produced pain. Unlike 14i (R), this compound had much lower water solubility. So to achieve an adequate total dose, the route was switched to SC for subsequent injections (SC behind neck, the tumors were SC bilateral, on the sides of the mouse midway between the legs). On an extended injection schedule, at a total dose of 615 mg/kg, 14h (R) produced a 3% T/C, 1.9 log kill (++ activity rating), confirming the activity of the R form of the compound. However, 14h (R) was less active and required a higher total dose than the parent compound, 11c (R) (400 mg/kg total dose), given IP on a similar extended schedule in Cage 11 (0% T/C, 3.3 log kill, 1/5 tumor free on day 148. This animal was then re-implanted with PO3/142. The tumor implants grew successfully, indicating no immunologic factors were involved with the original cure.

14i (R): Cage 2: A dose of 135 mg/kg was injected IP on day 3 only. No further injections were given due to the prolonged pain response produced by this route and dose post injection. The mice displayed hind-leg stretching and flattening for up to 1 hour post injection—a classic response to pain. There was a pronounced body weight loss of −1.6 g (−6.7%) on day 7 (nadir) with full recovery by day 9. Despite the low total dose delivered, 14i (R) was active by the IP route, producing a 10% T/C and a 1.1 log cell kill (+ activity rating).

Cage 3: A dose of 80 mg/kg was injected IP on day 3 only. As for Cage 2 above, further injections were discontinued due to the prolonged pain response produced (one hour duration). There was one injection death on day 4 (upper GI inflammation was noted at necropsy). Despite the low dose delivered, 14i (R) was active in this group as well although just barely (37% T/C, 0.7 log kill, + activity rating).

Cage 4: An initial dose of 50 mg/kg IP, given on day 3 did not cause any adverse reaction post injection. The route was switched to IV due to the significant pain produced by the higher doses, and injections continued on an every other day schedule (Q2d×7) through day 15 for a total dose of 455 mg/kg. A modest weight loss nadir of −0.8 g (−3.4%) occurred on day 7 with full recovery by day 11 (weight gain during treatment). This dose was moderately active (8% T/C, 1.6 log kill, ++ activity rating). Considering the modest weight loss, it is likely that substantially higher dosages could have been administered (which would have produced greater efficacy).

XK469 (R): Cage 5: SC injections of 80 mg/kg/inj were given qd 3–5 for a total dose of 240 mg/kg. Injections were stopped due to a significant −16.7% body weight loss (nadir occurred d9 with full recovery by d14). There was one drug death on day 10 (necropsy: diarrhea, liquid filled inflamed GI indicative of GI epithelial damage). This route/schedule was run to determine if XK469 (and the series) was active by the SC route. In hindsight, a lower dose given on an intermittent schedule may have been better tolerated. Nonetheless, XK469 (although at a LD20 dose on this schedule) was active by the SC route, producing a 9% T/C and a 1.6 log kill, ++ activity rating.

Cage 6: IP injections of 80 mg/kg/inj were given on days 3 and 5. Sporadic hind-leg stretching (transient pain) lasting 1–2 minutes post injection was noted. On days 7 and 9, the mice were not injected as they had a scruffy appearance, and sustained a body weight loss of −11.6% (nadir on day 9). Full weight recovery occurred on day 11 and injections were resumed on days 11 and 13 for a total of 320 mg/kg. XK469 was very active by the IP route on this schedule (5% T/C, 2.0 log cell kill, +++ activity rating).

Cage 7: IP injections of 50 mg/kg/inj were given on a Q2d×7 schedule starting on day 3 for a total dose of 350 mg/kg. This dose was well tolerated, with no adverse symptoms noted post injection. A body weight loss nadir of −0.8 g (−3.0%) occurred on day 8 with full recovery on day 11 (wt. gain during treatment). XK469 (R) was very active by the IP route on this extended intermittent schedule, producing a 5% T/C and a 2.2 log kill (+++ activity rating).

14h (R): Cage 8: An initial dose of 135 mg/kg was injected IP on day 3. There was transient puffiness and a pain reaction noted post injection so subsequent injections were given by the SC route. 14h (R) was injected SC on days 5 and 7 (135 mg/kg) with no reaction noted post injection. On day 9, the animals were rested due to a slightly scruffy appearance and a body weight loss (nadir d9) of −2.8 g (−11.6%). Although the mice did not fully recover their starting weight until day 20, they steadily gained weight and improved in appearance from day 10 on and so treatment resumed on day 11 (50 mg/kg), and continued on days 13 and 15 (80 mg/kg) for a total dose of 615 mg/kg. 14h (R) was active at this dose, producing a 3% T/C and a 1.9 log cell kill (++ activity rating).

Cage 9: IP injections of 80 mg/kg/inj were given on days 3, 5 and 7. Sporadic hind-leg stretching (transient pain) lasting 1–2 minutes post injection was noted. On day 9, the mice were rested due to a scruffy appearance and weight loss (nadir of −13.3% occurred on day 10). Although the mice did not fully recover their starting weight until day 20, they steadily gained weight and improved in appearance from day 11 on and so injections resumed on days 11, 13 and 15 for a total of 480 mg/kg. 14h (R) was also very active at this dose, producing a 6% T/C, and a 1.7 log cell kill, ++ activity rating).

Cage 10: IP injections of 50 mg/kg/inj were given on a Q2d×7 schedule starting on day 3 for a total dose of 350 mg/kg. This dose was well tolerated, with no adverse symptoms noted post injection. A moderate body weight loss nadir of −1.6 g (−6.6%) occurred on day 8 with full recovery on day 15 (wt. gain during treatment). 14h (R) was modestly active by the IP route on this extended intermittent schedule, producing a 16.5% T/C and a 1.0 log kill (+ activity rating).

11c (R): Cage 11: IP injections of 80 mg/kg/inj were given on days 3 and 5. Sporadic hind-leg stretching (transient pain) lasting 1–2 minutes post injection was noted. On days 7 and 9, the mice were rested due to a scruffy appearance and a pronounced body weight loss of −18% (nadir occurred on day 9). Although the mice did not fully recover their starting weight until day 16, they steadily gained weight and improved in appearance from day 11 on and so injections resumed on days 11, 13 and 15 for a total of 400 mg/kg. Although the weight loss sustained by these mice in this treatment group indicate a near LD10 dose (20% body weight loss is considered excessively toxic by NCI standards), 11c (R) was highly active by the IP route, producing a 0% T/C, and a 3.3 log cell kill, ++++ activity rating). One mouse remained tumor free to day 148, at which time the animal was re-implanted with PO3/142. The tumor implants grew successfully, indicating no immunologic factors were involved with the original cure.

Cage 12: IP injections of 50 mg/kg/inj were given on a Q2d×7 schedule starting on day 3 for a total dose of 350 mg/kg. This dose was well tolerated, with no adverse symptoms noted post injection. A moderate body weight loss of −0.8 g (−3.2%) occurred on day 8 (nadir) with full recovery on day 11 (wt. gain during treatment). 11c (R) was active by the IP route on this extended intermittent schedule, producing a 3% T/C and a 1.4 log kill (++ activity rating).

General Preparative Procedures

Preparation of {4-{(7-Substituted-2-quinolinyl)oxy}phenoxy} propionic acid compounds (Schemes I–II) As shown in Scheme I, a one-pot preparation of trans-3-ethoxyacryloyl chloride (3) by reaction of ethyl vinyl ether (1) and oxalyl chloride (2), with subsequent decarboxylation, has been described by Tietze et al., *Synthesis*, 1079–1080 (1993).

Scheme I

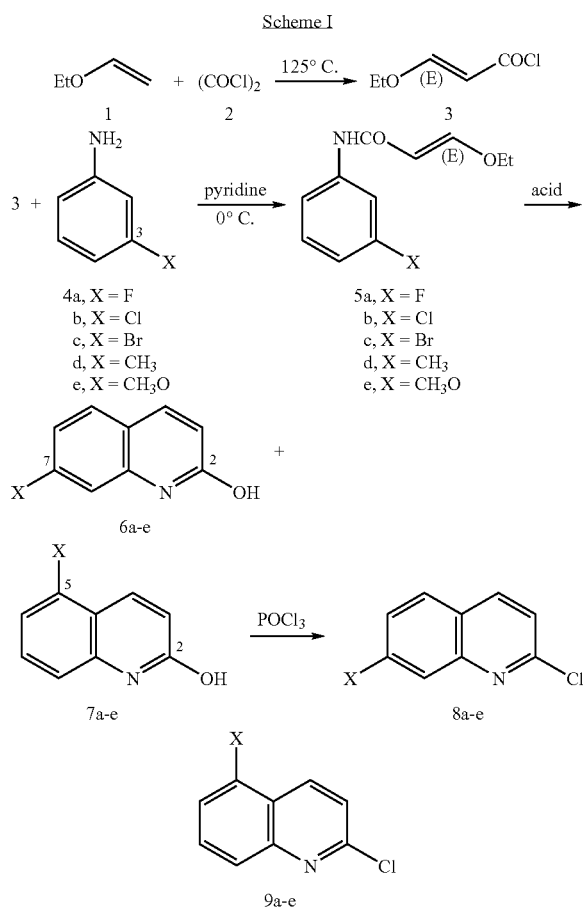

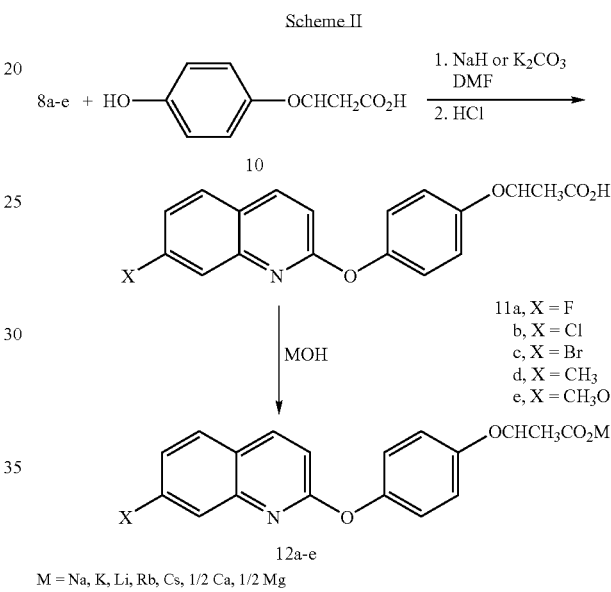

The amidation of the meta-substituted anilines (4a–e) with 3, i.e., the conversion to 5a–e, was modeled after the procedure described by Campbell and Roberts (U.S. Pat. No. 4,710,507) for preparation of trans-N-(4-bromo-3-methylphenyl)-3-ethoxypropenamide. Cyclization of the latter to a mixture of 5-(7a–e) and 7-substituted quinolin-2-ols (6a–e) was effected in either concentrated sulfuric or hydrochloric acid (Campbell and Roberts). The mixture, in turn, was transformed to the corresponding 2-chloroquinoline derivatives (8a–e) and (9a–e), on refluxing with phosphorous oxychloride (Campbell and Roberts). The majority of the 7-substituted derivatives (8a–e) separated from the regioisomer (9a–e) on fractional crystallization. The residue yielded additional 8a–c, following column chromatography over silica gel. As illustrated in Scheme II, the 2-chloroquinolines 8a–e were coupled with 2-(4-hydroxyphenoxy) propionic acid (20) using either NaH or $K_2CO_3$ in refluxing DMF followed by acidification to give the acids (21a–e) according to the following procedure. To a solution of the 7-substituted-2-chloroquinoline and 2-(4-hydroxyphenoxy) propionic acid (1 eq) dissolved in DMF (5 mL/mmol), 60% NaH (3 eq) was added in portions and the mixture heated at gentle reflux for 2 hours. After cooling it was concentrated to give a solid to which water was added and the solution was filtered through Celite, then washed with water. The filtrate was extracted with ether and the aqueous layer was acidified with 1M HCl to pH 3–4.

2-(4-Hydroxyphenoxy)propionic acid (1 eq) dissolved in DMF (5 mL/mmol), 60% NaH (3 eq) was added in portions and the mixture heated at gentle reflux for 2 hours. After cooling it was concentrated to give a solid to which water was added and the solution was filtered through Celite, then washed with water. The filtrate was extracted with ether and the aqueous layer was acidified with 1M HCl to pH 3–4. After cooling, the solid was collected, dried, dissolved in AcOEt and filtered through silica gel. The filtrate was concentrated to a small volume, the solid was collected and recrystallized from AcOEt-heptane to afford the propionic acid compounds (11a–e). The reaction can alternatively be carried out using $K_2CO_3$ (2.5 eq) instead of NaH but the reaction times are typically longer, for example, about 12 hours. These acids can also be converted to their metal salts (12a–e) by reacting with metal hydroxides.

$M = Na, K, Li, Rb, Cs, 1/2 Ca, 1/2 Mg$

XK469, which possesses a single stereogenic center at C-2 of the propionic acid moiety, is generally prepared in the form of a racemic mixture. The R-(+) forms of 11b and 11c were prepared by etherification of commercially available R-(+)-2-(4-hydroxyphenoxy)propionic acid with 8b and 8c. Chiral HPLC of the R-form of 11b and 11c, indicated that they had both been obtained in >99% ee. HPLC separations of both racemic 11b and 11c were carried out using ASTEC Chirobiotic T 250×4.6 mm, 65% $H_2O$, 35% $CH_3OH$, 20 mM $NH_4NO_3$ at 1 mL/min with detection at 250 nm. The same column, solvent system and spectral measurements were employed to determined the enantiomeric purity of (R–)-11b and (R–)-11c.

The invention will now be illustrated by the following non-limiting examples:

Preparation of {4-{(7-Substituted-2-quinolinyl) oxy}phenoxy} propionic amide compounds (A=CH) and {4-{(7-Substituted-2-quinoxalinyl)oxy}-phenoxy}propionic amide compounds (A=N) (Scheme III) A description of the conversion of representative 2-{4-((7-bromo and 7-chloro-2-quinolinyl)oxy)phenoxy}propionic acid compounds to their corresponding mono- and di-substituted propionamide derivatives follows. Compounds of formula 14 were prepared from the corresponding compounds of formula 13a–d using the reaction conditions illustrated below. The designation of specific substituents X, Y, A, Z, $R_a$ and $R_b$ in product compounds of formula 14a–i are listed in Table A.

The reaction of 2-{4-{(7-bromo-2-quinolinyl)oxy}phenoxy}propionic acid 11-c (A=CH) (Scheme II) with thionyl chloride generated the intermediate acid chloride, which on treatment with methylamine in THF, gave the monomethyl amide 14d (Table A) in good yield. Similarly, the reaction of the acid chloride of compound 11b (X=Cl, Y=H, A=CH) in THF with dimethylamine afforded the N,N'-dimethylamide 14e (Table A).

Treatment of the acid chlorides of (RS)-, or (R+)- or (S−)-, of compound XK469 (A=N) and compound 11c (A=CH), respectively, with the amino acid taurine ($NH_2CH_2CH_2SO_3H$) in THF and in the presence of 1M NaOH provided the corresponding {(RS)-, (R+)- or (S−)-} taurine compounds in good yield in the form of sodium salt (14f and 14g) in good yield. The same reactions with the amino acid glycine ($NH_2CH_2CO_2H$) can afford the N-amino acid derivative (14h and 14i of Table A).

Scheme III

XK469

13a-b

| Compound | X  | Y    | R   |
|----------|----|----- |-----|
| 11b      | Cl | H    | H   |
| 11c      | Br | H    | H   |
| 13a      | Cl | OCH₃ | H   |
| 13b      | Cl | H    | CH₃ |

| Starting Compound | Reaction Conditions | Product |
|-------------------|---------------------|---------|
| 13b               | MeOH/NH₃            | 14a     |
| XK469             | SOCl₂, NH₂CH₃/THF   | 14b     |
| 13b               | SOCl₂, NH(CH₃)₂/THF | 14c     |
| 11c               | SOCl₂, NH₂CH₃/THF   | 14d     |
| 11b               | SOCl₂, NH(CH₃)₂/THF | 14e     |
| XK469             | SOCl₂, NaOH/THF, NH₂(CH₂)₂SO₃H, H⁺ | 14f |
| 13a               | SOCl₂, NaOH/THF, NH₂(CH₂)₂SO₃H, H⁺ | 14g |
| 13a               | SOCl₂, NaOH/THF, NHCH₂C(=O)OM, H⁺  | 14h |
| XK469             | SOCl₂, NaOH/THF, NHCH₂C(=O)OM, H⁺  | 14i |

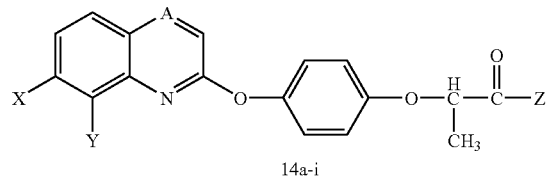

14a-i

TABLE A

Compounds prepared according to Scheme III.

| Compound | X  | Y    | A  | Z                                |
|----------|----|------|----|----------------------------------|
| 14a      | Cl | H    | N  | NH₂                              |
| 14b      | Cl | H    | N  | NHCH₃                            |
| 14c      | Cl | OCH₃ | N  | N(CH₃)₂                          |
| 14d      | Br | H    | CH | NHCH₃                            |
| 14e      | Cl | H    | CH | N(CH₃)₂                          |
| 14f      | Cl | H    | N  | NH(CH₂)₂SO₃M taurine salt        |
| 14g      | Br | H    | CH | NH(CH₂)₂SO₃M taurine salt        |
| 14h      | Br | H    | CH | NHCH₂CO₂M glycine salt           |
| 14i      | Cl | H    | N  | NHCH₂CO₂M glycine salt           |

EXAMPLE 1

2-{4-((7-Bromo-2-quinolinyl)oxy)phenoxy} propionmethylamide (14d) A mixture of 2-{4-[(7-bromo-2-quinolinyl)oxy]phenoxy}propionic acid 11c (0.20 g, 0.52 mmol) and SOCl₂ (0.40 mL, 0.66 g, 5.4 mmol) was heated for 1 h, then concentrated to give a yellowish solid. The latter was dissolved in THF (10 mL); methylamine (2 M in THF) was added until the mixture was basic and then concentrated to give a yellowish solid. Water (10 mL) and saturated NaHCO₃ were added until pH 8, and the mixture extracted with AcOEt (2×25 mL). The combined extracts were washed with saturated NaCl (10 mL) and after drying (MgSO₄), filtered through silica gel and concentrated to give an off white solid. The latter was recrystallized from EtOH-heptane to give the title compound 14d (0.20 g, 95%) as white crystals; mp 150–151° C.; ¹H NMR (400 MHz, CDCl₃) δ 8.06 (d, J=8.8 Hz, 1H), 7.93 (d, J=1.6 Hz, 1H), 7.59 (d, J=9.2 Hz, 1H), 7.48 (dd, J=8.4, 1.6 Hz, 1H), 7.19–7.14 (m, 2H), 7.07 (d, J=8.8 Hz, 1H), 6.97–6.91 (m, 2H), 6.56 (bs, 1H), 4.68 (q, J=6.4 Hz, 1H), 2.87 (d, J=5.2 Hz, 3H), 1.60 (d, J=6.4 Hz, 3H). ¹³C NMR (100 MHz, CDCl₃) δ 173.0, 162.6, 154.2, 148.0, 147.3, 139.8, 130.4, 128.8, 128.4, 124.4, 124.2, 123.1, 116.5, 113.3, 75.9, 26.2, 19.1. MS (EI) m/z (%) 400 (M⁺, 33), 342 (40), 328 (6), 316 (22), 298 (7), 206 (17), 189 (5), 149 (6), 137 (18), 127 (17), 121 (10), 109 (9), 95 (16), 86 (20), 81 (51), 69 (100), 57 (19), 55 (21), 45 (7). HRMS (EI) m/z 400.0426 (Calcd for C₁₉H₁₇N₂BrO₃ 400.0423).

EXAMPLE 2

2-{4-((7-Chloro-2-quinolinyl)oxy)phenoxy}propiondimethylamide (14e) A mixture of 2-{4-[(7-chloro-2-quinolinyl)oxy]phenoxy}propionic acid 13c (0.45 g, 1.3 mmol) and SOCl₂ (0.48 mL, 0.78 g, 6.6 mmol) was refluxed for 1 h. After cooling the solution was concentrated under reduced pressure to give a yellow liquid, which was dissolved in THF (15 mL). Dimethylamine (2 M in THF) was added until the mixture was basic and then concentrated to give a light brown solid. Water (15 mL) and saturated NaHCO₃ were added to pH 8 and the mixture extracted with AcOEt (2×25 mL). The combined extracts were washed with saturated NaCl (2×10 mL), and after drying (MgSO₄), were concentrated to give a yellow liquid. The latter was purified by flash column chromatography (1:4 hexanes:AcOEt) (R_f=0.44 (1:4 hexanes:AcOEt)) to give a white solid, which crystallized from EtOH-heptane to give the title compound 14e, (0.42 g, 87%) as an off white solid, mp 148–150° C.; $^1$H NMR (400 MHz, CDCl$_3$) δ 8.05 (d, J=9.2 Hz, 1H), 7.75 (d, J=2.4 Hz, 1H), 7.65 (d, J=9.2 Hz, 1H), 7.34 (dd, J=8.8, 2.4 Hz, 1H), 7.17–7.11 (m, 2H), 7.03 (d, J=8.0 Hz, 1H), 6.96–6.90 (m, 2H), 4.96 (q, J=6.4 Hz, 1H), 3.14 (s, 3H), 2.97 (s, 3H), 1.62 (d, J=7.2 Hz, 3H). $^{13}$C NMR (100 MHz, CDCl$_3$) δ 171.3, 162.8, 154.6, 147.6, 147.2, 139.6, 135.9, 128.7, 127.2, 125.8, 124.1, 122.9, 115.9, 113.0, 74.5, 36.8, 36.6, 17.9. IR (KBr) 1650, 1605, 1590, 1570, 1485, 1435, 1420, 1410, 1395, 1370, 1365, 1340, 1295, 1280, 1250, 1225, 1190, 1160, 1140, 1115, 1100, 1080, 1065, 1030, 1005, 990, 960, 940, 875, 850, 825, 805, 790, 770, 730, 625, 605, 505, 480, 450, 360 cm$^{-1}$. MS (EI) m/z (%) 370 (M$^{+b, 30}$), 298 (48), 270 (21), 254 (15), 236 (3), 220 (3), 191 (8), 135 (3), 127 (11), 105 (3), 100 (100), 91 (4), 72 (47), 69 (6), 57 (6), 55 (8), 44 (6), 28 (15). Anal. Calcd for C$_{20}$H$_{19}$N$_2$ClO$_3$: C, 64.78; H, 5.16; N, 7.55. Found: C, 64.55; H, 5.15; N, 7.47.

EXAMPLE 3

Sodium (2-(4-(7-chloro-2-quinoxalinyl)oxy)phenoxy)propionylamino ethanesulfonate (14f) A mixture of (XK469) (0.49 g, 1.4 mmol) and SOCl$_2$ (0.52 mL, 0.85 g, 7.1 mmol) was heated for 1 h before concentrating to give a yellow liquid, which was dissolved in THF (1.5 mL). The resulting solution and 1 M NaOH (1.6 mL, 1.6 mmol) were added dropwise at equal rates to a solution of sodium β-aminoethylsulfonate (taurine) (0.17 g, 1.3 mmol) in 1 M NaOH (1.4 mL, 1.4 mmol) at 0° C. After stirring for ½ h at rt the mixture was diluted with water (10 mL) and 1 M H$_2$SO$_4$ added until pH 3. The mixture was washed with ether (2×25 mL) and 1 M NaOH added to the aqueous layer until pH 7, before it was concentrated and dried to give a yellowish solid. The latter was triturated with hot CH$_3$OH and the insoluble material filtered off before the filtrate was concentrated and recrystallized from CH$_3$OH-EtOH to give the title compound 14f; (0.47 g, 74%) as white crystals, mp 250–252° C.; $^1$H NMR (400 MHz, CD$_3$OD) δ 8.68 (s, 1H), 7.99 (d, J=8.8 Hz, 1H), 7.71 (d, J=1.6 Hz, 1H), 7.61 (d, J=8.8 Hz, 1H), 7.21 (d, J=9.2 Hz, 2H), 7.06 (d, J=8.8 Hz, 2H), 4.72 (q, J=6.4 Hz, 1H), 3.74–3.58 (m, 2H), 3.03–2.88 (m, 2H), 1.57 (d, J=6.8 Hz, 3H). IR (KBr) 3260, 1650, 1565, 1550, 1500, 1485, 1440, 1395, 1370, 1330, 1290, 1260, 1230, 1195, 1140, 1105, 1090, 1055, 1000, 915, 835, 820, 805, 770, 695, 665, 635, 610, 530, 500, 430 cm$^{-1}$. MS (EI negative ion) m/z (%) 450 (M$^{-Na}$, 100), 343 (3).

Chiral HPLC separation (S enantiomer 19.6 minutes, R enantiomer 23.2 minutes) using Regis (R,R)-Whelk-O1 250×4.6 mm, 75% Hexanes, 25% 2—PrOH, 15 mM AcONH$_4$ at 1.5 mL/min with detection at 245 nm.

The same series of reactions was performed with compound XK469 (R+) or (S–), to produce the corresponding enantiomer of compound 14f; (R+) mp 250–252° C., [α]$_D$=+20.2° (c=0.50, H$_2$O); or (S–) 251–253° C., [α]$_D$=–20.0° (c=0.50, H$_2$O).

EXAMPLE 4

A. Racemic. Sodium (2-(4-(7-bromo-2-quinolinyl)oxy)phenoxy)propionylamino ethanesulfonate (14g) A mixture of compound 11c (X=7—Br; A=CH)(prepared according to *J. Med. Chem.*, 2002, 45, 3130, at 3135, see compound 11d) (0.23 g, 0.59 mmol) and SOCl$_2$ (0.45 mL, 0.73 g, 6.2 mmol) was heated for 1 h before concentrating to give a yellow solid which was dissolved in THF (2.0 mL). This solution and 1 M NaOH (0.7 mL, 0.7 mmol) were added dropwise to a solution of taurine (0.07 g, 0.55 mmol) in 1 M NaOH (0.6 mL, 0.6 mmol) at 0° C. After stirring for ½ h at rt the mixture was diluted with water (5 mL) and 1 M H$_2$SO$_4$ added until pH 3. The mixture was washed with ether (2×10 mL) and 1 M NaOH added to the aqueous layer until pH 7 before it was concentrated and dried to give the title compound 14g as an off-white solid. This was mixed with hot CH$_3$OH and the insoluble material filtered off before the filtrate was concentrated and recrystallized from CH$_3$OH to give (0.21 g, 75%) as off white crystals. mp 231–233° C.; $^1$H NMR (400 MHz, CD$_3$OD) δ 8.26 (d, J=9.2 Hz, 1H), 7.87 (d, J=1.6 Hz, 1H), 7.76 (d, J=8.0 Hz, 1H), 7.55 (dd, J=8.8, 1.6 Hz, 1H), 7.18–7.10 (m, 3H), 7.08–7.02 (m, 2H), 4.72 (q, J=6.4 Hz, 1H), 3.71–3.60 (m, 2H), 3.04–2.90 (m, 2H), 1.57 (d, J=7.6 Hz, 3H).

B. (R) enantiomer. Sodium (2-(4-(7-bromo-2-quinolinyl)oxy)phenoxy) propionylamino ethanesulfonate {14g (R)} The above procedure (A. Racemic) was repeated with the exception that compound 11c was obtained from etherification of 8c and commercially available R-(+)-2-(4-hydroxyphenoxy)propionic acid 10.

(R) enantiomer: mp 251–253° C., [α]$_D$=+20.0° (c=0.25, CH$_3$OH). Chiral HPLC separation (S enantiomer 21.8 minutes, R enantiomer 25.7 minutes) using Regis (R,R)-Whelk-O1 250×4.6 mm, 75% Hexanes, 25% 2-PrOH, 15 mM AcONH$_4$ at 1.5 mL/min with detection at 230 nm.

EXAMPLE 5

A. Racemic. {2-[4-(7-Bromo-quinolin-2-yloxy)-phenoxy]-propionylamino}acetic acid (14h). The procedure of Example 4 was repeated with the exception that a solution of glycine was substituted for a solution of taurine to provide the compound of the formula corresponding to 14h where R is H, that is, Z is —NHCH$_2$CO$_2$H, mp 157–159° C., or salts thereof).

B. (R) enantiomer. {2-[4-(7-Bromo-quinolin-2-yloxy)-phenoxy]-propionylamino}acetic acid (14h (R)). The above procedure (A. Racemic) was repeated with the exception that compound 11c was obtained from etherification of 8c and commercially available R-(+)-2-(4-hydroxyphenoxy) propionic acid 10.

(R) enantiomer: mp 172–174° C., [α]$_D$=+8.6° (c=0.50, CH$_3$OH). Chiral HPLC separation (S enantiomer 24.0 minutes, R enantiomer 29.0 minutes) using Regis (R,R)-Whelk-O1 250×4.6 mm, 65% Hexanes, 35% 2-PrOH, 15 mM AcONH$_4$ at 1 mL/min with detection at 220 nm.

EXAMPLE 6

A. Racemic {2-{4-(7-Chloro-quinoxalin-2-yloxy)-phenoxy} propionylamino}acetic acid (14i). The procedure of Example 3 was repeated with the exception that a solution of glycine was substituted for a solution of taurine to provide the compound of the formula corresponding to 14i where R is H, that is, Z is —NHCH$_2$CO$_2$H, mp 188–190° C., or salts thereof).

B. (R) enantiomer. {2-{4-(7-Chloro-quinoxalin-2-yloxy)-phenoxy}propionyl amino}acetic acid (14i (R)). The above procedure (A. Racemic) was repeated with the exception that XK469 was obtained from etherification with commercially available R-(+)-2-(4-hydroxyphenoxy)propionic acid 10.

(R) enantiomer: mp 190–192° C., $[\alpha]_D$=+19.0° (c=0.50, 0.1 M NaOH). Chiral HPLC separation (S enantiomer 21.7 minutes, R enantiomer 26.7 minutes) using Regis (R,R)-Whelk-O1 250×4.6 mm, 65% Hexanes, 35% 2-PrOH, 15 mM AcONH$_4$ at 1 mL/min with detection at 240 nm.

EXAMPLE 7

The following illustrates representative pharmaceutical dosage forms, containing a compound of formula I ('Compound X'), for therapeutic or prophylactic use in humans.

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0–7.5) | q.s. |
| Water for injection | q.s. ad 1 mL |

| (v) Injection 2 (10 mg/mL) | mg/ml |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 01 N Sodium hydroxide solution (pH adjustment to 7.0–7.5) | q.s. |
| Water for injection | q.s. ad 1 mL |

| (vi) Aerosol | mg/can |
|---|---|
| 'Compound X' | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

TABLE 1

Evaluation of Compound 14a and XK469 Against Early Stage Pancreatic Adenocarcinoma 03 in BDF$_1$ Male Mice

| Cage | Treatment/ Drug Route | Schedule | Total Dosage mg/kg | Mean Body Wt. Loss in g/mouse | Percent Body Wt. Loss | Day of Wt. Loss Nadir | Drug Deaths (days of death) | Median tumor burden in mg on day 14 (range) |
|---|---|---|---|---|---|---|---|---|
| 1 | No Rx | — | — | −0.4 | −1.8 | 5 | 0/5 | 1724 (580–2932) |
| 5 | 14a (PO) | QD3–6, 9–11 BID 7–8 | 1,320 | −0.8 | −3.6 | 8 | 0/5 | 126 (63–385) |
| 6 | 14a (PO) | QD3–6, 9–11 BID 7–8 | 660 | −0.4 | −1.8 | 5 | 0/5 | 695 (342–1389) |
| 7 | 14a (PO) | QD3–6, 9–11 BID 7–8 | 330 | −0.4 | −.8 | 6 | 0/5 | 1273 (343–1975) |
| 8 | XK469 (IV) | QD 3–5 | 180 | −3.6 | −15.5 | 8 | 0/5 | 189 (126–297) |

| Cage | Treatment/ Drug Route | T/C % | Tumor Free on day 21 | Time to 1000 mg days (range) | T-C (days) | Log Kill | Comments |
|---|---|---|---|---|---|---|---|
| 1 | No Rx | — | 0/5 | 11 (11–16) | — | — | — |
| 5 | 14a (PO) | 7.3 | 0/5 | 23 (21–35) | 12 | 1.9 | active (++) |

TABLE 1-continued

Evaluation of Compound 14a and XK469 Against Early Stage Pancreatic Adenocarcinoma 03 in BDF$_1$ Male Mice

| 6 | 14a (PO) | 40 | 0/5 | 15.5 (13–18.5) | 4.5 | 0.7 | active (+) |
| 7 | 14a (PO) | 74 | 0/5 | 13 (11.5–22) | 2 | 0.3 | inactive (--) |
| 8 | XK469 (IV) | 11 | 0/5 | 20 (18.5–23) | 9 | 1.4 | active (++) |

Mice: BDF1 Males;

DOB: Jun. 14, 1999;

DOA: Jul. 27, 1999;

Source: NIH: CRL-Raleigh;

Ave. Wt. = 22.8 g

Tumor: Pancreatic Adenocarcinoma P03/215;

DOT: Aug. 2, 1999;

Time to 1,000 mg = 11 days;

Td = 1.9 days

Preparation: Compound 14a: solid light yellow powder + 3% EtOH + 1% Tween-80 + dH$_2$O → suspension; pH = 5.5; 0.2 mL/mouse/inj.

XK469: (NIH:D697887, Lot#KS18-140-1): 90 mg/kg liquid stock diluted to 60 mg/kg with dH$_2$O→solution; pH = 8.0→6.5 with 1.0 N HCl; 0.2 mL/mouse/inj.

TABLE 2

Evaluation of Compound 14b Against Early Stage Pancreatic Ductal Adenocarcinoma #03

| Cage | Rx/Route | Sched | Total Dosage mg/kg | Mean Body Wt. Loss (g/mouse) | % Body Wt. Loss | Day of Wt. Loss Nadir | Drug Deaths (day of death) | Median Tumor Burden in mg on d18 (Range) |
|---|---|---|---|---|---|---|---|---|
| 1 | NoRx | — | — | 0 | 0 | 5 | — | 1713 (1295–2486) |
| 2 | XK469 (IV) | QD3–6, 10 | 300 | -3.2 | 15 | 8 | 0/5 | 64 (32–126) |
| 3 | 14b (PO) | BID3–7 | 2,300 | -2.0 | 9 | 8 | 0/5 | 671 (203–748) |
| 4 | 14b (PO) | BID 3, 4 | 480 | -0.8 | 4 | 5 | 0/5 | 1266 (895–1600) |
| 5 | 14b (PO) | BID 3 | 108 | +0.4 | 0 | 5 | 0/5 | 1312 (756–1387) |

| Cage | Rx/Route | T/C % | Tumor Free on d 154 | Time in days to 1000 mg (range) | Growth Delay (days) | Log Cell Kill | Activity Rating |
|---|---|---|---|---|---|---|---|
| 1 | NoRx | — | 0/5 | 13 (11–14) | — | | |
| 2 | XK469 (IV) | 4 | 1/5 | 41.1 (36.6–44.3) | 28.1 | 3.3 | ++++ Highly Active |
| 3 | 14b (PO) | 39 | 0/5 | 21 (19.5–38) | 7.0 | 0.8 | + Modestly Active |
| 4 | 14b (PO) | 74 | 0/5 | 15 (14.5–15) | 2.0 | 0.2 | – Inactive |
| 5 | 14b (PO) | 77 | 0/5 | 15.7 (13.8–19.8) | 2.7 | 0.3 | – Inactive |

Mice: BD$_1$ Female;

Source: CRL-Raleigh;

DOB: Jan. 24, 2000;

DOA: Feb. 29, 2000;

Av. Wts. = 21.6 g/mouse

Tumor: PO3/229;

DOT: Apr. 14, 2000;

Td = 2.6 days

Preparation: XK469 (Racemic, lot KS 18-140-1, NCI): White powder + 1% NaHCO$_3$ + PBS Solution; pH adjusted to 7.0 with HCl; 0.2 mL/mouse/inj;

Compound 14b: white powder + 5% EtOH, 3% POE + PBS Suspension; pH = 7; 0.2 mL/mouse/inj.

TABLE 3

Evaluation of Compound 14c Against Early Stage Mammary Adenocarcinoma 17/ADR

| Cage | Rx Cpd (Route) | # of Inj. | Total dose mg/kg | % Body Wt Loss at Nadir | Day of Nadir | Drug Deaths | Median Tumor Mass on Day 9 (Range) |
|---|---|---|---|---|---|---|---|
| 1 | No Rx | 0 | 0 | +1.4% | 7 | — | 1201 (1044–2220) |
| 2 | Adriamycin | 2 | 15 | −1.4% | 7 | 0/5 | 1086 (863–1506) |
| 4 | XK469 (IV) | 6 | 336 | −7.1% | 8 | 0/5 | 108 (63–270) |
| 5 | 14c (PO) | 6 | 870 | −5.8% | 9 | 0/5 | 243 (126–385) |
| 6 | 14c (PO) | 6 | 540 | +1.4% | 9 | 0/5 | 369 (234–466) |
| 7 | 14c (PO) | 6 | 334.8 | +0.0% | 9 | 0/5 | 368 (239–878) |
| 8 | 14c (PO) | 6 | 538.8 | −1.4% | 11 | 0/5 | 660 (271–835) |

| Cage | Rx Cpd (Route) | % T/C mass | Growth Delay in Days | Log Kill | Tumor Free day-21 | Activity Rating |
|---|---|---|---|---|---|---|
| 1 | No Rx | — | — | — | 0/5 | — |
| 2 | Adriamycin | 90% | 0 | none | 0/5 | −− |
| 4 | XK469 (IV) | 9% | 15.5 | 4.2 | 0/5 | ++++ |
| 5 | 14c (PO) | 20% | 5.5 | 1.5 | 0/5 | ++ |
| 6 | 14c (PO) | 31% | 5.0 | 1.4 | 0/5 | ++ |
| 7 | 14c (PO) | 31% | 3.5 | 1.0 | 0/5 | + |
| 8 | 14c (PO) | 55% | 3.3 | 0.9 | 0/5 | + |

Mice = C3H/He females
Source NCI CRL-Kingston
DOB = Dec. 13, 1999
DOA = Jan. 25, 2000
Avg. Wt = 27.6 gm
Tumor = Mammary Adenocarcinoma-17/Adr, a p-glycoprotein positive multi-drug resistant tumor/pass-194
DOT = Mar. 20, 2000
Td 1.1 days
File = 2586

TABLE 4

Evaluation of Compounds 11b, 14e, and XK469 Against Early Stage Pancreatic Ductal Adenocarcinoma 03 in female BDF1 mice.

| Cage | Rx (Route) | # of Inj. | Total dose mg/kg | % Body Wt Loss at Nadir | Day of Nadir | Drug Deaths | Median Tumor Mass on Day 14 (Range) |
|---|---|---|---|---|---|---|---|
| 1 | No Rx | 0 | 0 | +12% | 10 | — | 1513 (681–2149) |
| 2 | 14e (PO) | 14 | 1680 | +4.3 | 9 | 0/5 | 126 (63–264) |
| 3 | 14e (PO) | 14 | 840 | +3.3 | 10 | 0/5 | 234 (75–333) |
| 4 | 14e (PO) | 14 | 420 | 0 | 9 | 0/5 | 567 (446–1200) |
| 5 | XK469 (IV) | 7 | 399 | −6.7% | 8 | 0/5 | 63 (0–214) |
| 6 | XK469 (IV) | 7 | 266 | −6.7% | 5 | 0/5 | 126 (0–234) |
| 14 | 11b (IV) | 7 | 336 | −8.9% | 11 | 0/5 | 0 (0–126) |

| Cage | Rx (Route) | % T/C mass | Growth Delay in Days | Log Kill | Tumor Free day-37 | Activity Rating |
|---|---|---|---|---|---|---|
| 1 | No Rx | — | — | — | 0/5 | — |
| 2 | 14e (PO) | 8.3% | 16.5 | 2.5 | 0/5 | +++ |
| 3 | 14e (PO) | 15% | 14.5 | 2.2 | 0/5 | +++ |
| 4 | 14e (PO) | 37% | 3.5 | 0.5 | 0/5 | ± |
| 5 | XK469 (IV) | 4.1% | 11.5 | 1.7 | 0/5 | ++ |

TABLE 4-continued

Evaluation of Compounds 11b, 14e, and XK469 Against Early Stage Pancreatic Ductal Adenocarcinoma 03 in female BDF1 mice.

| 6 | XK469 (IV) | 8.3% | 9.5 | 1.4 | 0/5 | ++ |
| 14 | 11b (IV) | 0% | 17.5 | 2.6 | 0/5 | +++ |

Mice = BDF1 females
Source NCI-Raleigh
DOB = Mar. 27, 2000
DOA = May 9, 2000
Av. Wt. = 18.2 gm
Tumor = Pancreatic Ductal Adenocarcinoma 03/ pass-231
DOT = May 19, 2000
Td = 2.0 days
File = 2606
This tumor is highly sensitive to Taxol (++++ activity rating).
It is nicely sensitive to Adriamycin (+++ activity).
It is moderately sensitive to VP-16, Cytoxan, CisDDPt (++ activity rating).
It is modestly responsive to 5-FU (+ activity).
It is insensitive to Vinblastine.
Preparation: XK469 (R): white solid: 1% bicarb + PBS gave a solution, pH = 7.5; 0.2 mL/inj IV, QD 3–9;
Compound 14e: white solid + 6% ethanol + 3% POE80 + dH2O gave a suspension, pH = 4.5; 0.2 mL/inj PO BID days 3–9; and
Compound 11b: white solid + 1% bicarb + PBS gave a solution, pH = 7.5; 0.2 mL/inj IV, QD 3–9

TABLE 5

Evaluation of Compound 14f Against Early Stage Pancreatic Ductal Adenocarcinoma #03

| Cage | Treatment Compound (Drug Route) | Schedule | Total Dosage mg/kg | Mean Body Wt. Loss in g/mouse | Percent Body Wt. Loss | Day of Wt. Loss Nadir | Drug Death (day of death) | Median Tumor Burden in mg on d17 (range) |
|---|---|---|---|---|---|---|---|---|
| 1 | No Rx | — | — | +0.8 | +3.5 | 11 | — | 1202 (235–1666) |
| 2 | XK469 (R) (IV) | qd 3–10 | 360 | −1.6 | −1.6 | 11 | 0/5 | 256 (216–554) |
| 3 | 14f (IV-SC) | qd 3–5, 8–11 BID 6, 7 | 780 | +0.0 | +0.0 | 11 | 0/5 | 126 (63–322) |
| 4 | 14f (IV-SC) | ↓ | 390 | +0.8 | +3.5 | 11 | 0/5 | 600 (108–726) |
| 5 | 14f (IV) | qd 3, 4 | 30 | +1.6 | +7.1 | 11 | 0/5 | 1420 (446–1574) |

| Cage | Treatment Compound (Drug Route) | T/C % | Tumor Free on d35 | Time to 1000 mg in days (range) | T-C (days) | Log Cell Kill | Comments |
|---|---|---|---|---|---|---|---|
| 1 | No Rx | — | 0/5 | 16 (14–22) | — | — | — |
| 2 | XK469 (R) (IV) | 21 | 0/5 | 27 (20–30) | 11.0 | 1.84 | Active (++) |
| 3 | 14f (IV-SC) | 10 | 0/5 | 26 (24–31) | 10.0 | 1.67 | Active (++) |
| 4 | 14f (IV-SC) | 50 | 0/5 | 19.5 (18–26) | 3.5 | 0.58 | Inactive (−−) |
| 5 | 14f (IV) | >100 | 0/5 | 16 (14–23) | 0.0 | 0.0 | Inactive (−−) |

Mice: $C_{57}$ females
Source: NCI Frederick
DOB: Oct. 22, 2001
DOA: Dec. 4, 2001
Av. Wt. = 22 g/mouse
Tumor: Panc 03/124
DOT: Feb. 1, 2002
Td = 1.8 days
Preparation: XK469 (R): 99.4% (R) liquid stock + 0.5% $NaHCO_3$ + PBS → solution (pH = 7.5); 0.2 mL/mouse/inj;
Compound 14f: off white solid + $dH_2O$ → solution (pH = 5.5), 0.2 mL/mouse/inj.

TABLE 6

Evaluation of Compounds 14f (R) and 14f (S) Against
Early Stage Human Melanoma LOX in Balb/c females

| Cage | Cpd (Config) (Admin Route) | Schedule | Total Dosage mg/kg | Mean Body Wt. Loss in g/mouse | Percent Body Wt. Loss | Day of Wt. Loss Nadir | Drug Death (day of death) | Median Tumor Burden in mg on d 9 (Range) |
|---|---|---|---|---|---|---|---|---|
| 1 | No Rx | — | — | +1.2 | +5.9 | 7 | — | 1394 (1057–1674) |
| 2 | 14f (R) (IV) | qd 1–6 BID 7 | 700 | −2.8 | 13.5 | 13 | 0/5 | 651 (63–1114) |
| 3 | 14f (S) (IV) | qd 1–6 BID 7 | 700 | +0.4 | 2.0 | 8 | 0/5 | 994 (734–1200) |
| 4 | XK469 (R) (IV) | qd 1–7 | 175 | −1.6 | 8.0 | 7 | 0/5 | 467 (234–1067) |

| Cage | Cpd(Config) (Admin Route) | T/C % | Tumor Free on d 18 | Time to 1000 mg days (range) | T-C (days) | Log Cell Kill | Comments |
|---|---|---|---|---|---|---|---|
| 1 | No Rx | — | 0/5 | 8.0 (8.0–9.0) | — | — | Inactive (−−) |
| 2 | 14f (R) (IV) | 47 | 0/5 | 11.0 (8.5–23.5) | 3.0 | 0.8 | Active (+) |
| 3 | 14f (S) (IV) | 71 | 0/5 | 9.0 (8.0–10.0) | 1.0 | 0.3 | Inactive (−−) |
| 4 | XK469 (R) (IV) | 34 | 0/5 | 11.3 (9.0–13.0) | 3.3 | 0.8 | Active (+) |

Mice: Balb/c SCID
Source: NCI- Frederick
DOB: Nov. 26, 2001–Dec. 3, 2001
DOA: Jan. 8, 2002
Ave wt: 20.3 g/mouse
Tumor: Human Melanoma LOX/39S
DOT: Apr. 8, 2002
Td: 1.2 days
Preparation: XK469 (R): (98.4 enan. excess); 0.5% NaHCO$_3$ + PBS → solution (pH = 9 + 1N HCl –> pH = 7); 0.2 mL/mouse/inj.;
Compound 14f (R): white solid + dH$_2$O → solution (pH = 5.5); 0.2 mL/mouse/inj.; and
Compound 14f (S): white solid + dH$_2$O → solution (pH = 5.5); 0.2 mL/mouse/inj.

TABLE 7

Evaluation of Compound 14g Racemic, XK469 (R), and 11c
(R) Against Early Stage Mammary Adenocarcinoma 16/C

| Cg | Treatment | Drug Route | Schedule | Total Dosage mg/kg | Mean Body Wt. Loss in g/mouse | Percent Body Weight Loss | Day of Wt. Loss Nadir | Drug Death (day of death) | Median Tumor Burden in mg on d 9 (range) |
|---|---|---|---|---|---|---|---|---|---|
| 1 | No Rx | — | — | — | +0.8 | 0.0 | 4 | — | 1656 (1418–2526) |
| 2 | 14g (Racemic) | IV | BID 1–5 | 600 | −2.3 | −11.0 | 4 | 0/6 | 230 (0–728) |
| 3 | XK469 (R) | IV | qd 1–5 | 250 | −4.4 | −21.2 | 7 | 0/5 | 63 (0–365) |
| 4 | 11c (R) | IV | qd 1–5 | 240 | −6.0 | −29.4 | 9 | 1/5 (10) | 0 (all zeros) |

| Cg | Treatment | T/C % | Tumor Free on d 161 | Time to 1,000 mg in days (range) | T-C (days) | Log Cell Kill | Comments |
|---|---|---|---|---|---|---|---|
| 1 | No Rx | — | 0/5 | 8 (7–8) | — | — | — |
| 2 | 14g (Racemic) | 14 | 1/6 | 11.5 (9.5–13) | 3.5 | 0.9 | Active (+) |

TABLE 7-continued

Evaluation of Compound 14g Racemic, XK469 (R), and 11c
(R) Against Early Stage Mammary Adenocarcinoma 16/C

| | | | | | | | |
|---|---|---|---|---|---|---|---|
| 3 | XK469 (R) | 4 | 0/5 | 14.5 (12.5–19) | 6.5 | 1.6 | TOXIC |
| 4 | 11c (R) | 0 | 0/5 | 15.2 (13–17) | 7.2 | 1.8 | TOXIC |

Mice: $C_3H$ females;

Source: CRL - Kingston;

DOB: Mar. 18, 2002;

DOA: Apr. 22, 2002;

Av. Wt. = 20.6 g/mouse

Tumor: Mammary 16/C/204;

DOT: May 6, 2002;

Td = 1.2 days

Preparation

Compound 14g Racemic: white solid + $dH_2O$ + heat → solution (pH = 7); 0.2 ml/mouse/inj.

Compound XK469 (R): white solid + 0.5% $NaHCO_3$ (by volume) + $dH_2O$ → solution (pH = 10→7 w/1 N HCl); 0.2 ml/mouse/inj.

Compound 11c (R): white solid + 0.5% $NaHCO_3$ (by volume) + $dH_2O$ → solution; (pH = 10→7 w/1 N HCl); 0.2 ml/mouse/inj.

TABLE 8

Evaluation of Compounds 14f (R), 11c (R), and XK469
(R) Against Early State Mammary Adenocarcinoma 16/c.

| Cg | Treatment | Drug Route | Schedule | Total Dosage mg/kg | Mean Body Wt. Loss in g/mouse | Percent Body Weight Loss | Day of Wt. Loss Nadir | Drug Death (day of death) | Median Tumor Burden in mg on day 7 (range) |
|---|---|---|---|---|---|---|---|---|---|
| 1 | NoRx | — | — | — | +1.6 | +5.8 | 7 | — | 1820 (1286–2736) |
| 2 | 11c (R) | IV | Q2Dx8 | 480 | −1.2 | −4.3 | 14 | 0/5 | 0 (all zero) |
| 3 | XK469 (R) | IV | Q2Dx8 | 480 | −2.0 | −7.4 | 18 | 0/5 | 0 (all zero) |
| 4 | 14f (R) | IV | d1, 3–5, 7, 9, 11, 13, 15 | 1610 | −0.8 | −3.0 | 14 | 0/5 | 0 (0–151) |
| 5 | 14f (R) | IV | d1, 3–7, 9 | 665 | −0.8 | −2.9 | 5 | 0/5 | 260 (0–523) |

| Cg | Treatment | T/C % | Tumor Free on d28 | Time to 1000 mg in days (range) | T-C (days) | Log Cell Kill | Comments |
|---|---|---|---|---|---|---|---|
| 1 | NoRx | — | 0/5 | 6 (all d6) | — | — | — |
| 2 | 11c (R) | 0 | 0/5 | 22 (20–24) | 16 | 4.8 | Active (++++) |
| 3 | XK469 (R) | 0 | 0/5 | 24 (19–26) | 18 | 5.4 | Active (++++) |
| 4 | 14f (R) | 0 | 0/5 | 20 (16.5–22) | 14 | 4.2 | Active (++++) |
| 5 | 14f (R) | 14 | 0/5 | 12 (10–16.5) | 6 | 1.8 | Active (++) |

Mice: $C_3H$/HeN MTV(−) females;

Source: NCI-Frederick;

DOB: Aug. 19, 2002;

DOA: Oct. 1, 2002;

Av. Wt. = 27.6 g/mouse;

Tumor: Mam16/C/73;

DOT: Nov. 4, 2002;

Td = 1.0 day

Preparation:

Compound 11c (R): white solid + 3% EtOH + 1% POE + 0.25% $NaHCO_3$ (by volume) + $dH_2O$ → solution (pH = 9 → 7 w/1N HCl); 0.2 ml/mouse/inj. IV.

Compound XK469 (R): white solid + 3% EtOH + 1% POE + 0.25% $NaHCO_3$ (by volume) + $dH_2O$ → solution (pH = 7.5); 0.2 ml/mouse/inj. IV.

Compound 14f (R): white solid + $dH_2O$ → solution (pH = 5); 0.2 ml/mouse/inj. IV.

TABLE 9

Evaluation of Compounds 14g (R) and 11c (R) Against Early Stage Pancreatic Ductal Adenocarcinoma 03.

| Cg | Treatment | Drug Route | Schedule | Total Dosage mg/kg | Mean Body Wt. Loss in g/mouse | Percent Body Weight Loss | Day of Wt. Loss Nadir | Drug Death (day of death) | Median Tumor Burden in mg on d14 (range) |
|---|---|---|---|---|---|---|---|---|---|
| 1 | NoRx | — | — | — | +2.0 | +10.0 | 9 | — | 1004 (550–1093) |
| 2 | 14g (R) | IP | BID3–5 | 450 | −4.4 | −23.4 | 9 | 1/5 (10) | 0 (0–63) |
| 3 | 14g (R) | IP | BID3–7 | 450 | −1.2 | −6.7 | 9 | 0/5 | 126 (100–252) |
| 4 | 11c (R) | IP | Qd3–7 | 260 | −3.2 | −16.7 | 10 | 1/5 (14) | 126 (0–298) |
| 5 | 11c (R) | IP | Qd3–7 | 157.5 | −0.0 | −0.0 | 9 | 0/5 | 260 (75–351) |

| Cg | Treatment | T/C % | Tumor Free on d31 | Time to 1000 mg in days (range) | T-C (days) | Log Cell Kill | Comments |
|---|---|---|---|---|---|---|---|
| 1 | NoRx | — | 0/5 | 14 (13–18) | — | — | — |
| 2 | 14g (R) | 0 | 0/5 | 24.75 (23–27) | 10.75 | 1.52 | LD20 |
| 3 | 14g (R) | 12.6 | 0/5 | 26 (20–27) | 12 | 1.72 | Active (++) |
| 4 | 11c (R) | 12.6 | 0/5 | 24.5 (19–26) | 10.5 | 1.5 | LD20 |
| 5 | 11c (R) | 26 | 0/5 | 25 (22.5–26) | 11 | 1.58 | Active (++) |

Mice: $C_{57}$ females;
Source: NCI-Frederick;
DOB: Jul 29, 2002;
DOA: Sep. 17, 2002;
Av. Wt. = 18.5 g/mouse;
Tumor: Panc 03/135;
DOT: Sep. 27, 2002;
Td = 2.1 days
Preparation:
Compound 14g (R): white solid + 3% EtOH + 1% POE + $dH_2O$ → solution (pH = 7); 0.5 ml/mouse/inj. IP.
Compound 11c (R): white solid + 3% EtOH + 1% POE + 0.25% $NaHCO_3$ (by volume) + $dH_2O$ → solution (pH = 9.5 → 7 w/1N HCl); 0.5 ml/mouse/inj. IP.

TABLE 10

Evaluation of Compounds 14h (R), 14i (R), 11c (R), and XK469 (R), Against Early Stage Pancreatic Ductal Adenocarcinoma 03.

| Cage | Treatment | Drug Route | Schedule | Total Dosage mg/kg | Mean Body Wt. Loss in g/mouse | Percent Body Weight Loss | Day of Wt. Loss Nadir | Drug Death (day of death) | Median Tumor Burden in mg on d17 (range) |
|---|---|---|---|---|---|---|---|---|---|
| 1 | No Rx | — | — | — | +2.4 | +10.0 | 10 | — | 1838 (691–2457) |
| 2 | 14i (R) | IP | d 3 | 135 | −1.6 | −6.7 | 7 | 0/5 | 189 (0–615) |
| 3 | ↓ | ↓ | ↓ | 80 | −0.5 | −2.0 | 4 | 1/5 (d4) | 675 (108–1302) |
| 4 | ↓ | IP IV | d3 Q2d: 5–15 | 455 | −0.8 | −3.4 | 7 | 0/5 | 151 (126–196) |
| 5 | XK469 (R) | SC | Qd3–5 | 240 | −4.0 | −16.7 | 9 | 1/4 (d10) | 171 (63–529) |
| 6 | ↓ | IP | d3, 5, 11, 13 | 320 | −2.8 | −11.6 | 8 | 0/5 | 88 (0–352) |
| 7 | ↓ | ↓ | Q2d: 3–15 | 350 | −0.8 | −3.0 | 8 | 0/5 | 235 (0–428) |
| 8 | 14h (R) | IP SC | d 3 d5, 7, 11, 13, 15 | 615 | −2.8 | −11.6 | 9 | 0/5 | 63 (0–171) |
| 9 | ↓ | IP | d3, 5, 7, 11, 13, 15 | 480 | −3.2 | −13.3 | 10 | 0/5 | 108 (0–171) |

TABLE 10-continued

Evaluation of Compounds 14h (R), 14i (R), 11c (R), and XK469 (R), Against Early Stage Pancreatic Ductal Adenocarcinoma 03.

| 10 | ↓ | ↓ | Q2d: 3–15 | 350 | −1.6 | −6.6 | 8 | 0/5 | 304 (63–427) |
| 11 | 11c (R) | IP | d3, 5, 11, 13, 15 | 400 | −4.4 | −18.0 | 9 | 0/5 | 0 (0–108) |
| 12 | ↓ | ↓ | Q2d: 3–15 | 350 | −0.8 | −3.2 | 8 | 0/5 | 63 (0–309) |

| Cage | Treatment | T/C % | Tumor Free on 148 | Time to 1000 mg in days (range) | T-C (days) | Log Cell Kill | Comments |
|---|---|---|---|---|---|---|---|
| 1 | No Rx | — | 0/5 | 15 (12–19) | — | — | — |
| 2 | 14i (R) | 10 | 0/5 | 22.5 (19–26) | 7.5 | 1.1 | Active (+) |
| 3 | ↓ | 37 | 0/5 | 20 (16–29.5) | 5 | 0.7 | Active (+) |
| 4 | ↓ | 8 | 0/5 | 26 (23–30) | 11 | 1.6 | Active (++) |
| 5 | XK469 (R) | 9 | 0/5 | 26 (19–29.5) | 11 | 1.6 | Active (+) |
| 6 | ↓ | 5 | 0/5 | 29 (25–29) | 14 | 2.0 | Active (+++) |
| 7 | ↓ | 13 | 0/5 | 30 (26–31) | 15 | 2.2 | Active (+++) |
| 8 | 14h (R) | 3 | 0/5 | 28 (28–40) | 13 | 1.9 | Inactive (++) |
| 9 | ↓ | 6 | 0/5 | 27 (26–44) | 12 | 1.7 | Active (++) |
| 10 | ↓ | 16.5 | 0/5 | 22 (21.5–28) | 7 | 1.0 | Active (+) |
| 11 | 11c (R) | 0 | 1/5 | 38 (36–50) | 23 | 3.3 | Active (++++) |
| 12 | ↓ | 3 | 0/5 | 25 (22.5–30) | 10 | 1.4 | Active (++) |

Mice: $BDF_1$ males;

Source: CRL-Raleigh;

DOB: Aug. 26, 2002;

DOA: Oct. 8, 2002;

Av. Wt. = 23.5 g/mouse;

Tumor: PO3/135;

DOT: Oct. 18, 2002;

Td = 2.1 days

Preparation:

Compound 14h (R): white solid + 3% EtOH + 1% POE + 0.25% $NaHCO_3$ + saline → suspension (pH = 8.0); 0.5 ml/mouse/inj, IP; 0.2 ml/mouse/inj, SC.

Compound 14i (R): white solid + 3% EtOH + 1% POE + 0.25% $NaHCO_3$ + saline → solution (pH = 8.0); 0.5 ml/mouse/inj, IP; 0.2 ml/mouse/inj, IV.

Compound XK469 (R): white solid + 3% EtOH + 1% POE + 0.5% $NaHCO_3$ + saline → solution (pH = 9 → 7 with 1N HCl); 0.2 ml/mouse/inj, SC; 0.5 ml/mouse/inj, IP.

Compound 11c (R): white solid + 3% EtOH + 1% POE + 0.25% $NaHCO_3$ + saline → solution (pH = 9 → 7 with 1N HCl); 0.5 ml/mouse/inj, IP.

What is claimed is:

1. A compound of formula (I):

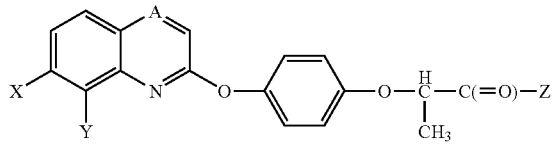

(I)

wherein
A is CH;
X is F, Cl, or Br;
Y is hydrogen, hydroxy, or (C$_1$–C$_7$)alkoxy; and
Z is an amino acid, or heterocycle;
or a pharmaceutically acceptable salt thereof.

2. The compound of claim 1, wherein Y is H.
3. The compound of claim 1, wherein Y is —OH.
4. The compound of claim 1, wherein Y is —OMe.
5. The compound of any of claims 1 to 4 wherein X is —Cl.
6. The compound of any of claims 1 to 4 wherein X is —Br.
7. The compound of any of claims 1 to 6 wherein Z is an amino acid.
8. The compound of any of claims 1 to 6 wherein Z is —NH—(CH$_2$)$_2$—SO$_3$H.
9. The compound of any of claims 1 to 6 wherein Z is —NH—CH$_2$—CO$_2$H.
10. The compound of any of claims 1 to 6 wherein Z is —NH—CH(CH$_3$)—CO$_2$H.
11. The compound of any of claims 1 to 6 wherein Z is a nitrogen linked pyrrolidino, piperidino, morpholino, 1,3-benzodiazepino, 1,4-benzodiazepino, or 1,5-benzodiazepino.
12. A compound of formula (I):

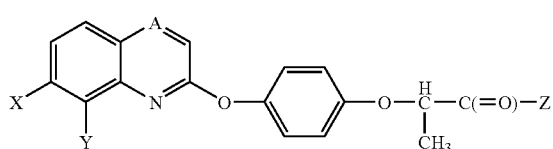

(I)

wherein
A is CH;
X is F, Cl, or Br;
Y is hydroxy, or (C$_1$–C$_7$)alkoxy; and
Z is an —NR$_a$R$_b$;
where R$_a$ and R$_b$ is independently hydrogen, (C$_1$–C$_7$) alkyl, (C$_1$–C$_7$)alkanoyl, aryl, aryl(C$_1$–C$_7$)alkyl, or where R$_a$ and R$_b$ together with the nitrogen to which they are attached are a pyrrolidino, piperidino, morpholino, 1,3-benzodiazepino, 1,4-benzodiazepino, or 1,5-benzodiazepino;
or a pharmaceutically acceptable salt thereof.

13. The compound of claim 12, wherein Y is —OH.
14. The compound of claim 12, wherein Y is —OMe.
15. The compound of any of claims 12 to 14 wherein X is —Cl.
16. The compound of any of claims 12 to 14 wherein X is —Br.
17. The compound of any of claims 12 to 16 wherein Z is —NR$_a$R$_b$.
18. The compound of any of claims 12 to 16 wherein Z is —NH$_2$.
19. The compound of any of claims 12 to 16 wherein Z is —NHCH$_3$.
20. The compound of any of claims 12 to 16 wherein Z is a nitrogen linked 1,3-benzodiazepino, 1,4-benzodiazepino, or 1,5-benzodiazepino.
21. A compound of formula (I):

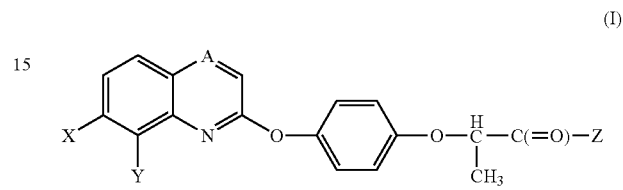

(I)

wherein
A is CH;
X is F, Cl, or Br;
Y is hydrogen, hydroxy, or (C$_1$–C$_7$)alkoxy; and
Z is —NR$_a$R$_b$;
R$_a$ and R$_b$ are each independently hydrogen, (C$_1$–C$_7$) alkyl, (C$_1$–C$_7$)alkanoyl, aryl, aryl(C$_1$–C$_7$)alkyl, or where R$_a$ and R$_b$ together with the nitrogen to which they are attached are a pyrrolidino, piperidino, morpholino, 1,3-benzodiazepino, 1,4-benzodiazepino, or 1,5-benzodiazepino;
or a pharmaceutically acceptable salt thereof.

22. The compound of claim 21 wherein R$_a$ and R$_b$ are each independently (C$_1$–C$_7$)alkanoyl, aryl, aryl(C$_1$–C$_7$)alkyl, or where R$_a$ and R$_b$ together with the nitrogen to which they are attached are a pyrrolidino, piperidino, morpholino, 1,3-benzodiazepino, 1,4-benzodiazepino, or 1,5-benzodiazepino.
23. The compound of claim 21 or 22 wherein Y is H.
24. The compound of claim 21 or 22 wherein Y is —OH.
25. The compound of claim 21 or 22 wherein Y is —OMe.
26. The compound of any of claims 21 to 25 wherein X is —Cl.
27. The compound of any of claims 21 to 25 wherein X is —Br.
28. The compound of any of claims 21 to 27 wherein Z is —NR$_a$R$_b$.
29. The compound of any of claims 21 to 27 wherein Z is a nitrogen linked pyrrolidino, piperidino, or morpholino.
30. The compound of any of claims 21 to 27 wherein Z is a nitrogen linked 1,3-benzodiazepino, 1,4-benzodiazepino, or 1,5-benzodiazepino.
31. The compound
2-{4-((7-Bromo-2-quinolinyl)oxy)phenoxy}propionmethylamide;
2-{4-((7-Chloro-2-quinolinyl)oxy)phenoxy}propiondimethylamide;
2-{4-((7-Bromo-2-quinolinyl)oxy)phenoxy}propionylamino ethanesulfonic acid;
{2-{4-(7-Bromo-2-quinolin-2-yloxy)phenoxy}propionylamino}ecetic acid;
(R) (2-(4-(7-Bromo-2-quinolinyl)oxy)phenoxy)propionylamino ethanesulfonic acid;

(R) {2-[4-(7-Bromo-quinolin-2-yloxy)-phenoxy]propionylamino}acetic acid;

or pharmaceutically acceptable salts thereof.

32. The compound of any of claims 1 to 30 or 31 which is the (R) enantiomer.

33. The compound of any of claims 1 to 30 or 31 which is the (S) enantiomer.

34. The compound of any of claims 1 to 30 or 31 to 33, wherein the compound is isolated and purified.

35. The compound of claim 34, wherein the compound is a solid.

36. The compound of claim 34, wherein the compound is a crystalline solid.

37. A pharmaceutical composition comprising a compound any one of claims 1 to 30 or 31 to 36 and a pharmaceutically acceptable diluent or carrier.

38. The pharmaceutical composition of claim 37, wherein the pharmaceutical composition is formulated as a unit dosage form.

39. The pharmaceutical composition of claim 38, wherein the unit dosage form is formulated for oral administration.

40. The pharmaceutical composition of claim 38, wherein the unit dosage form is formulated for administration by injection.

* * * * *